(12) United States Patent
Xiong et al.

(10) Patent No.: US 10,481,127 B2
(45) Date of Patent: Nov. 19, 2019

(54) APPARATUS FOR, SYSTEM FOR AND METHODS OF MAINTAINING SENSOR ACCURACY

(71) Applicant: Ecolab USA Inc., St. Paul, MN (US)

(72) Inventors: Kun Xiong, Naperville, IL (US); Brandon M. Davis, Oswego, IL (US); William A. Von Drasek, Oak Forest, IL (US)

(73) Assignee: Ecolab USA Inc., Saint Paul, MN (US)

( * ) Notice: Subject to any disclaimer, the term of this patent is extended or adjusted under 35 U.S.C. 154(b) by 100 days.

(21) Appl. No.: 15/714,592

(22) Filed: Sep. 25, 2017

(65) Prior Publication Data

US 2018/0017522 A1  Jan. 18, 2018

Related U.S. Application Data

(62) Division of application No. 14/594,589, filed on Jan. 12, 2015, now Pat. No. 9,772,303.

(51) Int. Cl.
| | |
|---|---|
| *G01N 33/18* | (2006.01) |
| *G01N 27/416* | (2006.01) |
| *G01N 27/38* | (2006.01) |
| *G01N 1/34* | (2006.01) |

(52) U.S. Cl.
CPC ..... *G01N 27/4168* (2013.01); *G01N 27/4167* (2013.01); *G01N 33/18* (2013.01); *G01N 1/34* (2013.01); *Y10T 436/12* (2015.01)

(58) Field of Classification Search
CPC .............. G01N 33/18; G01N 27/4167; G01N 27/4168; G01N 1/34; B08B 3/02; B08B 5/02; Y10T 436/115831; Y10T 436/118497; Y10T 436/12; Y10T 436/204998; Y10T 436/25875
USPC .............. 436/50, 52, 55, 108, 133, 163, 181
See application file for complete search history.

(56) References Cited

U.S. PATENT DOCUMENTS

| | | |
|---|---|---|
| 4,138,638 A | 2/1979 | Amano et al. |
| 4,307,741 A | 12/1981 | Rossi |
| 4,517,849 A | 5/1985 | Nakahori et al. |
| 4,609,874 A | 9/1986 | Reich |
| 6,475,394 B2 | 11/2002 | Xiong et al. |

(Continued)

FOREIGN PATENT DOCUMENTS

| | | |
|---|---|---|
| CN | 201259491 Y | 6/2009 |
| CN | 101587088 A | 11/2009 |

(Continued)

OTHER PUBLICATIONS

Analytical Technology, Inc., "pH/ORPMonitor: Model Q46P/R," Aug. 2013, 6 pp., Collegeville, PA.

(Continued)

*Primary Examiner* — Maureen Wallenhorst
(74) *Attorney, Agent, or Firm* — Fredrikson & Byron, P.A.

(57) ABSTRACT

Methods of maintaining accuracy in the measurement of one or more parameters of industrial water in industrial water systems are provided. The methods include the use of physical and/or chemical procedures to prevent and/or remove deposition from one or more surfaces utilized in measurement of the one or more parameters. The deposition may be caused by, for example, corrosion, fouling, or microbiological growth.

20 Claims, 12 Drawing Sheets

(56) References Cited

U.S. PATENT DOCUMENTS

| | | | |
|---|---|---|---|
| 6,840,251 B2* | 1/2005 | Gill | A61L 2/16 134/22.1 |
| 7,981,679 B2 | 7/2011 | Rice | |
| 8,429,952 B1 | 4/2013 | Bringhurst et al. | |
| 8,668,779 B2* | 3/2014 | Cooper | A61L 2/16 134/22.1 |
| 9,772,303 B2* | 9/2017 | Xiong | G01N 33/18 |
| 9,810,676 B2* | 11/2017 | Xiong | G01N 33/18 |
| 2002/0108911 A1 | 8/2002 | Xiong et al. | |
| 2004/0060576 A1 | 4/2004 | Cronin et al. | |
| 2011/0056276 A1 | 3/2011 | Scott et al. | |
| 2013/0186188 A1 | 7/2013 | Bradley et al. | |
| 2013/0191064 A1 | 7/2013 | Park et al. | |
| 2013/0240440 A1 | 9/2013 | Maung et al. | |
| 2013/0293881 A1 | 11/2013 | Tokhtuev et al. | |
| 2016/0202155 A1 | 7/2016 | Xiong et al. | |
| 2016/0202229 A1 | 7/2016 | Xiong et al. | |
| 2019/0041376 A1* | 2/2019 | Hinchman | B05B 12/004 |

FOREIGN PATENT DOCUMENTS

| | | |
|---|---|---|
| CN | 202599942 U | 12/2012 |
| CN | 203886863 U | 10/2014 |
| GB | 2110382 A | 6/1983 |
| GB | 2295232 A | 5/1996 |
| KR | 10-2010-0048485 A | 5/2010 |

OTHER PUBLICATIONS

Israel Patent Office, International Search Report in International Patent Application No. PCT/US2016/012949, dated May 18, 2016, 6 pp.

Israel Patent Office, Written Opinion in International Patent Application No. PCT/US2016/012949, dated May 18, 2016, 6 pp.

Israel Patent Office, International Search Report in International Patent Application No. PCT/US2016/012955, dated Apr. 18, 2016, 4 pp.

Israel Patent Office, Written Opinion in International Patent Application No. PCT/US2016/012955, dated Apr. 18, 2016, 4 pp.

Turner Designs, "Little Dipper In-Line Fluorometer," May 24, 2013, 17 pp., Sunnyvale, CA.

European Patent Office, Extended European Search Report in European Patent Application No. 16737692.0, 5 pp. (dated Oct. 10, 2018).

* cited by examiner

APPARATUS FOR, SYSTEM FOR AND METHODS OF MAINTAINING SENSOR ACCURACY

CROSS-REFERENCE TO RELATED APPLICATION

This application is a divisional of U.S. patent application Ser. No. 14/594,589, filed Jan. 12, 2015, and granted as U.S. Pat. No. 9,772,303 on Sep. 26, 2017, the entire contents of which are incorporated by reference.

BACKGROUND

Many industrial water systems require precise chemical treatment for any one or combination of the following: maintaining superior energy transfer, reducing waste, protecting assets, and improving product quality. Precise chemical treatment can be administered to an industrial water system by monitoring characteristic variables such as, e.g., conductivity, pH, oxidation-reduction potential, microorganism concentration, alkalinity, and hardness.

Measured changes in any of these variables can provide input into controlling process operations. For example, a measured increase in conductivity of cooling water circulating in a cooling tower operation may trigger a blow down of the operation followed by addition of make-up water, thereby reducing the conductivity of the cooling water. Maintaining accurate, precise measurement of characteristic variables of an industrial water system, particularly a cooling water system, is key to its efficient treatment and operation.

For industrial water systems, more particularly cooling water systems, three issues are generally addressed by treatment operations: 1) Inhibition of scaling caused by mineral deposition, e.g., calcium carbonate and/or magnesium silicate; 2) Inhibition of fouling caused by deposition of suspended deposits caused by, e.g., corrosion; and 3) Inhibition of microbial contamination caused by, e.g., bacteria, algae, and/or fungi. Any of these conditions may cause deposits to form on wetted surfaces, particularly surfaces that are utilized in measurement of a parameter of the industrial water system. Deposition of any of these onto a measurement surface are of particular concern, as deposition can introduce measurement error (inaccuracy, imprecision, or both) caused by, e.g., delayed measurement response time, measurement drift (e.g., changing offset), or measurement instability.

Several sensor probe cleaning devices and methods are available. For example, ultrasonic cleaning techniques exist for liquid systems comprising dissolved gases. Mechanical wiping systems have been implemented in some applications. Air jet, water jet, and off-line chemical treatments have been used as well.

SUMMARY

Methods of maintaining accuracy in measuring a parameter of an industrial water system are provided. In an aspect, the method comprises contacting a liquid stream at a liquid stream pressure with a surface utilized for measuring a parameter with a sensor. A gaseous stream is introduced into the liquid stream, thereby causing the combined gaseous and liquid stream to contact the surface. The gaseous stream is introduced into the liquid stream at a gaseous pressure of from about 10 psi to about 100 psi greater than the liquid stream pressure.

In a further aspect, the method comprises contacting an industrial water stream at an industrial water stream pressure with at least one of a wetted surface of a pH sensor and a wetted surface of an oxidation-reduction potential sensor. The pH and/or oxidation-reduction potential of the industrial water stream is measured. A cleaning solution comprising urea hydrogen chloride is contacted with at least one of the wetted surfaces for a first period of time and at a concentration sufficient to clean the at least one of the wetted surfaces. The industrial water stream is re-contacted with the cleaned at least one of the wetted surfaces at the industrial water stream pressure for a second period of time, thereby measuring pH and/or oxidation-reduction potential of the industrial water stream using cleaned pH and/or oxidation-reduction potential sensors. A recovery curve is created that is related to the measured pH and/or the measured oxidation-reduction potential using the cleaned pH and/or oxidation-reduction potential sensors. The aforementioned steps are repeated. The respective recovery curves are compared. If the comparison of the respective recovery curves demonstrates acceptable sensor degradation, the respective sensor may remain in service. However, if the respective sensor demonstrates unacceptable sensor degradation, the respective sensor is removed from service.

In yet another aspect, the method comprises contacting an industrial water stream at an industrial water stream pressure with at least one of a wetted surface of a pH sensor and a wetted surface of an oxidation-reduction potential sensor. A cleaning solution is contacted with at least one of the wetted surface of the pH sensor and the wetted surface of the oxidation-reduction potential sensor. The industrial water stream is re-contacted with at least one of the wetted surface of the pH sensor and the wetted surface of the oxidation-reduction potential sensor at the industrial water stream pressure. A gaseous stream is introduced into the industrial water stream at a gaseous stream pressure of from about 10 psi to about 100 psi greater than the industrial water stream pressure and after initiation of the re-contacting.

A method of maintaining accuracy in the measurement of a plurality of parameters of industrial water in an industrial water system is also provided. The method comprises contacting an industrial water stream at an industrial water stream pressure with a plurality of surfaces utilized for measuring a plurality of parameters with a plurality of sensors. A first subset of the surfaces is isolated from the industrial water stream while a second subset of the surfaces maintains contact with the industrial water stream. At least one surface of the first subset is cleaned while the second subset maintains contact with the industrial water stream. Contact with the industrial water stream is restored with the first subset of surfaces. The first subset of surfaces comprises at least one of a wetted surface of a light transference medium, a wetted surface of a pH sensor, and a wetted surface of an oxidation-reduction potential sensor. The second subset of surfaces comprises at least one of a wetted surface of a corrosion detection sensor and a wetted surface of a conductivity sensor.

In a further aspect, an apparatus for maintaining accuracy in the measurement of a parameter of industrial water is provided. The apparatus comprises a body having a top portion, a bottom portion, an entry portion, and an exit portion. The apparatus includes at least one sensor aperture formed into the top portion and extending partially through the body toward the bottom portion. The at least one sensor aperture is configured to accept at least one sensor for measuring the parameter of industrial water. The apparatus includes a liquid flow bore formed through the body between the entry portion and the exit portion. The liquid flow bore fluidly communicates with the at least one sensor aperture and configured to allow a liquid stream to flow through the body. The apparatus includes a gas flow bore formed at least partially through the body. The gas flow bore is configured to allow a gaseous stream to flow into the body. The apparatus also includes at least one jet channel formed in the body and fluidly connecting the gas flow bore and the liquid flow bore. The at least one jet channel terminates in the liquid flow bore substantially opposite the at least one sensor aperture so as to direct the gaseous stream from the gas flow bore into the liquid flow bore toward the at least one sensor aperture.

In yet another aspect, an industrial water measuring system is provided. The system comprises an apparatus configured to maintain accuracy in the measurement of a parameter of industrial water. The apparatus comprises a body having a top portion, a bottom portion, an entry portion, and an exit portion. The apparatus includes a liquid flow bore formed through the body between the entry portion and the exit portion. The liquid flow bore is configured to allow a liquid stream to flow through the body. The apparatus includes at least one sensor aperture formed into the top portion of the body and extending at least partially through the body to fluidly communicate with the liquid flow bore at a sensor opening of the at least one sensor aperture. The apparatus also includes a gas flow bore formed at least partially through the body. The gas flow bore is configured to allow a gaseous stream to flow into the body. The apparatus includes at least one jet channel formed in the body and fluidly connecting the gas flow bore and the liquid flow bore. The at least one jet channel terminates in the liquid flow bore substantially opposite the sensor opening of the at least one sensor aperture. The system also includes at least one sensor disposed in the at least one sensor aperture. The at least one sensor includes a surface disposed in the sensor opening so as to sense a parameter of the liquid stream flowing through the liquid flow bore. The at least one jet channel is configured to direct at least a portion of the gaseous stream from the gas flow bore into the liquid flow bore toward the surface of the sensor disposed in the sensor opening of the at least one sensor aperture so as to clean the surface of the sensor.

In another aspect, an apparatus for maintaining accuracy in the measurement of a parameter of industrial water is provided. The apparatus comprises a body having a top portion, a bottom portion, an entry portion, and an exit portion. The apparatus includes a liquid flow bore formed through the body between the entry portion and the exit portion. The liquid flow bore is configured to allow a liquid stream to flow through the body. The apparatus includes a first sensor aperture formed into the top portion substantially perpendicular to the liquid flow bore and extending partially through the body to fluidly communicate with the liquid flow bore at a first sensor opening. The first sensor aperture is configured to accept a first sensor for measuring the parameter of industrial water. The apparatus includes a second sensor aperture formed into the top portion substantially perpendicular to the liquid flow bore and extending partially through the body to fluidly communicate with the liquid flow bore at a second sensor opening. The second sensor aperture is configured to accept a second sensor for measuring a parameter of industrial water. The apparatus includes a gas flow bore formed at least partially through the body substantially parallel to the liquid flow bore. The gas flow bore is configured to allow a gaseous stream to flow into the body. The apparatus includes a first jet channel formed in the body substantially perpendicular to the liquid flow bore and fluidly connecting the gas flow bore and the liquid flow bore. The first jet channel terminates in the liquid flow bore substantially opposite the first sensor opening of the first sensor aperture so as to direct at least a portion of the gaseous stream from the gas flow bore into the liquid flow bore toward the first sensor opening. The apparatus includes a second jet channel formed in the body substantially perpendicular to the liquid flow bore and fluidly connecting the gas flow bore and the liquid flow bore. The second jet channel terminating in the liquid flow bore substantially opposite the second sensor opening of the second sensor aperture so as to direct at least a portion of the gaseous stream from the gas flow bore into the liquid flow bore toward the second sensor opening.

BRIEF DESCRIPTION OF THE SEVERAL VIEWS OF THE DRAWING(S)

DETAILED DESCRIPTION

Figure 1A:
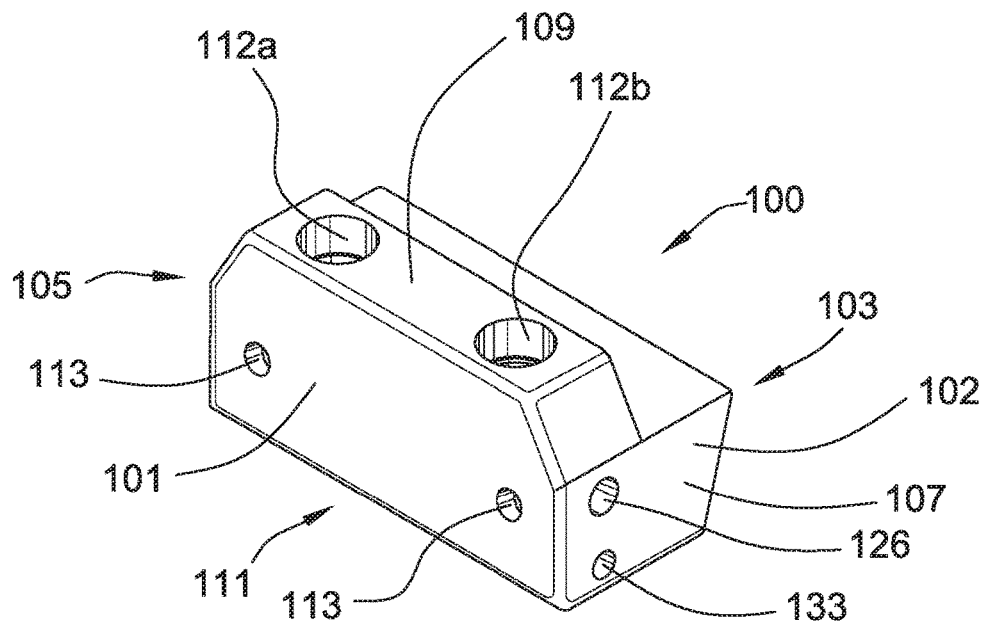
FIG. 1a illustrates a perspective view of an apparatus that may be used to perform methods of the present disclosure.

While embodiments encompassing the general inventive concepts may take various forms, there is shown in the drawings and will hereinafter be described various illustrative and preferred embodiments with the understanding that the present disclosure is to be considered an exemplification and is not intended to be limited to the specific embodiments.

Generally, methods of maintaining accuracy in the measurement of a parameter of industrial water, which may be cooling water, are provided. "Cooling water" refers to a liquid substance comprising water that is circulated through a system of one or more conduits and heat exchange equipment thereby transferring heat energy from one substance to another. The substance that loses heat is said to be cooled, and the one that receives heat is referred to as the coolant.

A general goal of conducting the methods disclosed herein is to maintain accuracy in measurements performed in monitoring and optionally controlling industrial water systems by way of preventing deposition onto a surface critical to performing said measurements. Another general goal of conducting the methods disclosed herein is to remove deposition from surfaces critical to performing said measurements, thereby restoring accuracy that may have been lost because of the deposition. The deposition may be due to scaling, fouling, microbiological growth, or combinations thereof.

A more specific goal of conducting the methods disclosed herein is to prevent deposition onto at least one of a wetted surface of a pH sensor, a wetted surface of an oxidation-reduction potential sensor, and a wetted surface of a light transference medium used in an industrial water system, thereby maintaining an acceptable level of accuracy in measurements made from the utilized sensor(s). Another more specific goal of conducting the methods disclosed herein is to remove deposition onto at least one of a wetted surface of a pH sensor, a wetted surface of an oxidation-reduction potential sensor, and a wetted surface of a light transference medium used in an industrial water system, thereby restoring a level of accuracy that may have been lost because of the deposition.

As it pertains to this disclosure, unless otherwise indicated, "industrial water" refers to a liquid or a mixed state substance comprising a liquid, wherein the liquid comprises water, and wherein the liquid or mixed state substance is used for an industrial purpose. By way of example, a non-exhaustive list of industrial purposes includes the following: heating, cooling, manufacturing (e.g., papermaking), refining, chemical processing, crude oil extraction, natural gas extraction, and the like. "Cooling water" is an exemplary embodiment of "industrial water."

As it pertains to this disclosure, unless otherwise indicated, "continuous(-ly)" describes performance of an action for an extended period of time without interruption. An exemplary "extended period of time" is 24 hours.

As it pertains to this disclosure, unless otherwise indicated, "pH sensor" refers to an electrode-type sensor utilized for measuring pH of a liquid, which may or may not include a dedicated input device, a dedicated output device, or a dedicated input-output device. An exemplary embodiment of a pH sensor is Part No. 400-C0060.88, available from Nalco, an Ecolab Company, 1601 West Diehl Road, Naperville, Ill. 60563 (http://ecatalog.nalco.com/pH-Meters-Waterproof-C739.aspx). Certain pH sensors may measure parameters in addition to pH.

As it pertains to this disclosure, unless otherwise indicated, "oxidation-reduction potential sensor" refers to an electrode-type sensor utilized for measuring oxidation-reduction potential ("ORP") of a liquid, which may or may not include a dedicated input device, a dedicated output device, or a dedicated input-output device. An exemplary embodiment of an oxidation-reduction potential sensor is Part No. 400-P1342.88, available from Nalco, an Ecolab Company, 1601 West Diehl Road, Naperville, Ill. 60563 (http://ecatalog.nalco.com/ORP-Pocket-Meter-Waterproof-C732.aspx). Certain oxidation-reduction potential sensors may measure parameters in addition to oxidation-reduction potential. Examples of other sensors, such as conductivity sensors and corrosion monitors, are also available from Nalco, an Ecolab Company, 1601 West Diehl Road, Naperville, Ill. 60563 (Nalco online Equipment Catalog can be found at the following url: http://ecatalog.nalco.com/Default.aspx).

As it pertains to this disclosure, unless otherwise indicated, a "period of time" (e.g., a "first period of time"), when in reference to contacting a cleaning solution to a wetted surface of a sensor (e.g., pH sensor, oxidation-reduction potential sensor, etc.), refers to, for example, a period of time sufficient to remove at least a portion of, or substantially all, obstruction that may be found on the wetted surface of the sensor in contact with the cleaning solution, at a particular concentration of cleaning solution. Exemplary ranges of periods of time for contacting the wetted surface of the sensor with a cleaning solution include, but are not limited to, from about 1 second, or from about 10 seconds, or from about 30 seconds, or from about 1 minute, to about 2 minutes, or to about 3 minutes, or to about 5 minutes, or to about 10 minutes, or to about 30 minutes, or to about 1 hour, including from about 1 minute to about 5 minutes, and including from about 1 minute to about 10 minutes, and including from about 1 minute to about 1 hour. The period of time sufficient to clean a wetted surface using the methods of the present disclosure may vary depending on factors including, inter alia, the chemical species of the cleaning solution, the concentration of the cleaning solution, temperature, pressure, flow rate, turbulence, and the like.

As it pertains to this disclosure, unless otherwise indicated, "controller" refers to an electronic device having components such as a processor, memory device, digital storage medium, cathode ray tube, liquid crystal display, plasma display, touch screen, or other monitor, and/or other components. Controllers include, for example, an interactive interface that guides a user, provides prompts to the user, or provides information to the user regarding any portion of the method of the invention. Such information may include, for example, building of calibration models, data collection of one or more parameters, measurement location(s), management of resulting data sets, etc.

When utilized, the controller is preferably operable for integration and/or communication with one or more application-specific integrated circuits, programs, computer-executable instructions or algorithms, one or more hard-wired devices, wireless devices, and/or one or more mechanical devices such as liquid handlers, hydraulic arms, servos, or other devices. Moreover, the controller is operable to integrate feedback, feed-forward, or predictive loop(s) resulting from, inter alia, the parameters measured by practicing the method(s) of the present disclosure. Some or all of the controller system functions may be at a central location, such as a network server, for communication over a local area network, wide area network, wireless network, extranet, the Internet, microwave link, infrared link, and the like, and any combinations of such links or other suitable links. In addition, other components such as a signal conditioner or system monitor may be included to facilitate signal transmission and signal-processing algorithms.

By way of example, the controller is operable to implement the method of the invention in a semi-automated or fully-automated fashion. In another embodiment, the controller is operable to implement the method in a manual or semi-manual fashion. Examples of the aforementioned variations of the invention are provided herein in reference to the figures.

For example, a dataset collected from a liquid may include variables or system parameters such as oxidation-reduction potential, pH, concentrations of certain chemical species or ions (e.g., determined empirically, automatically, fluorescently, electrochemically, colorimetrically, measured directly, calculated, etc.), temperature, turbidity, pressure, flow rate, dissolved or suspended solids, etc. Such parameters are typically measured with any type of suitable data measuring/sensing/capturing equipment, such as pH sensors, ion analyzers, temperature sensors, pressure sensors, corrosion detection sensors, and/or any other suitable device or method. Devices capable of detecting or sensing colorimetric, refractometric, spectrophotometric, luminometric, and/or fluorometric signals are of particular utility for the present invention. Such data capturing equipment is preferably in communication with the controller and, according to alternative embodiments, may have advanced functions (including any part of control algorithms described herein) imparted by the controller.

Data transmission of any of the measured parameters or signals to a user, chemical pumps, alarms, or other system components is accomplished using any suitable device, such as a wired or wireless network, cable, digital subscriber line, internet, etc. Any suitable interface standard(s), such as an Ethernet interface, wireless interface (e.g., IEEE 802.11a/b/g/n, 802.16, Bluetooth, optical, infrared, other radiofrequency, any other suitable wireless data transmission method, and any combinations of the foregoing), universal serial bus, telephone network, the like, and combinations of such interfaces/connections may be used. As used herein, the term "network" encompasses all of these data transmission methods. Any of the components, devices, sensors, etc., herein described may be connected to one another and/or the controller using the above-described or other suitable interface or connection. In an embodiment, information (collectively referring to all of the inputs or outputs generated by the method of the invention) is received from the system and archived. In another embodiment, such information is processed according to a timetable or schedule. In a further embodiment, such information is processed in real-time. Such real-time reception may also include, for example, "streaming data" over a computer network.

As it pertains to this disclosure, unless otherwise indicated, "control scheme" refers to providing output from a controller based on input to the controller as defined herein.

A method of maintaining accuracy in measuring a parameter of an industrial water system is provided. The method comprises contacting a liquid stream at a liquid stream pressure with a surface utilized for measuring a parameter with a sensor. A gaseous stream is introduced into the liquid stream, thereby causing the combined gaseous and liquid stream to contact the surface. The gaseous stream is introduced into the liquid stream at a gaseous pressure of from about 10 psi to about 100 psi greater than the liquid stream pressure.

Figure 1B:
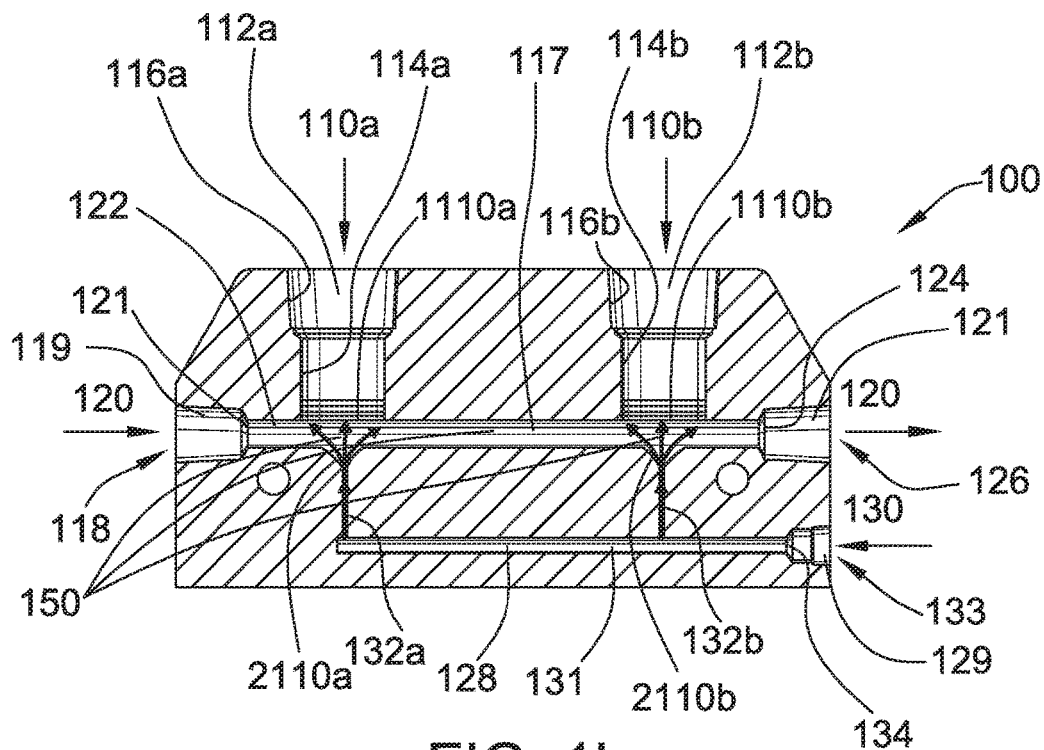
FIG. 1b illustrates a sectional view of an apparatus that may be used to perform methods of the present disclosure.

FIGS. 1a and 1b illustrate an embodiment of an apparatus that may be used to carry out at least a portion of one or more of the inventive methods described herein. In certain embodiments, apparatus 100 can be used as an industrial water measuring system for measuring and for maintaining accuracy of measurements of at least one parameter of industrial water used in an industrial water system. FIG. 1a shows a perspective view of apparatus 100, while FIG. 1b shows a more detailed sectional view of apparatus 100. As shown, apparatus 100 comprises body 102 that is capable of supporting two sensors, pH sensor 110a and oxidation-reduction potential sensor 110b. However, a person of ordinary skill in the art will recognize that apparatus 100 can be designed and built to implement one, two, or any reasonable number of sensors 110, that the positions of pH sensor 110a and oxidation-reduction potential sensor 110b can be swapped, or apparatus 100 may implement two pH sensors 110a or two oxidation-reduction potential sensors 110b. Additionally, it is contemplated that other suitable types of sensors can be used. As shown in the figures, the sensors 110a, 110b can be supported within first sensor aperture 112a and second sensor aperture 112b formed in body 102.

Figure 1C:
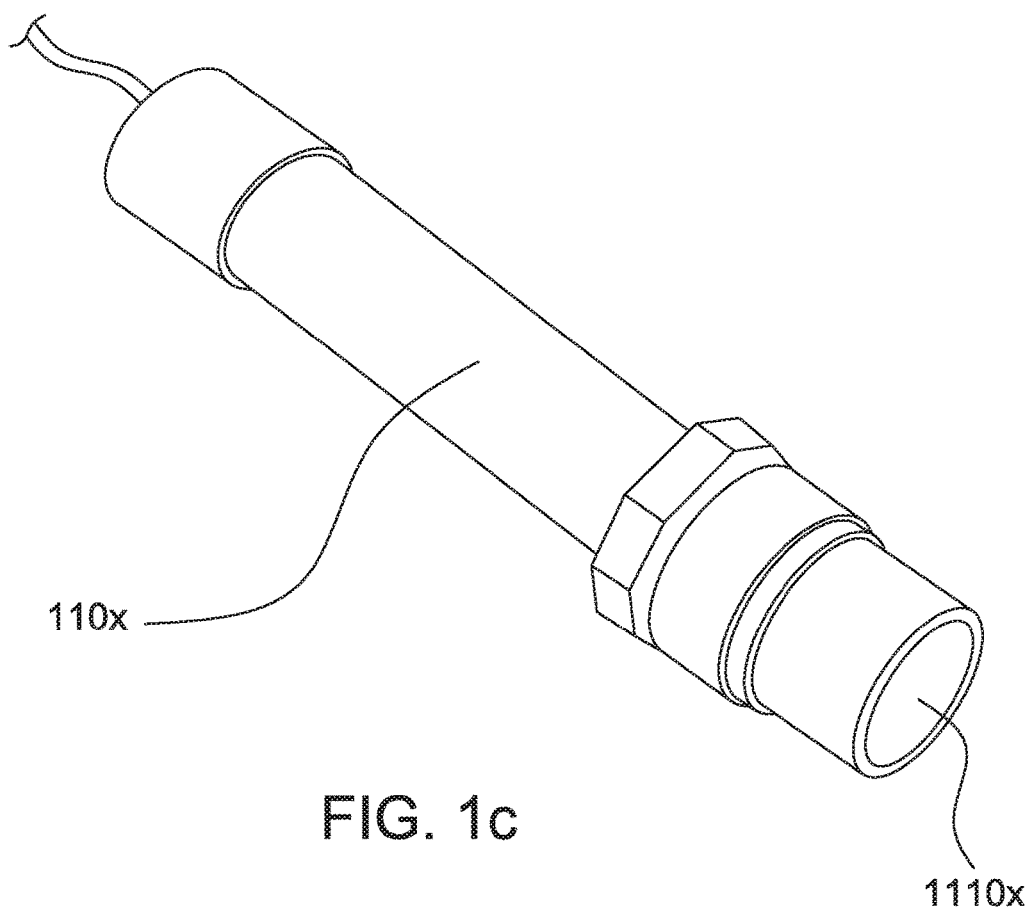
FIG. 1c illustrates an embodiment of an optical sensor that may be used to perform methods of the present disclosure.

Furthermore, FIG. 1c illustrates an embodiment of an optical sensor 110x, e.g., an embodiment of a fluorometer. In the embodiment of FIG. 1c, optical sensor 110x may be operably mounted in place of at least one of pH sensor 110a and oxidation-reduction potential sensor 110b, using, e.g., apparatus 100. Optical sensor 110x may utilize an optical window or a reflective surface as its wetted surface 1110x, as described herein. As is the case with pH sensor 110a and oxidation-reduction potential sensor 110b, a person of skill in the art will recognize that apparatus 100 provides merely an embodiment of an apparatus that may be utilized to carry out the methods disclosed herein, or portions thereof, and that the present application should not be limited to apparatus 100. The term "optical window" is used to refer to a barrier that allows for optical observation of a substance in a process. The optical observation may be visually or electronically performed. Optical observation refers to any light-based form of observation. Examples of optical observation include, but are not limited to, fluorometry, absorption, spectrophotometry, imaging, and any combination thereof.

Referring again to FIG. 1a, body 102 of apparatus 100 includes front portion 101, rear portion 103, entry portion 105, exit portion 107, top portion 109, and bottom portion 111. In some embodiments, fastener channels 113 are formed through body 102 between front portion 101 and rear portion 103 to accommodate fasteners, for example, bolts or screws. The first and second sensor apertures 112a, 112b are formed into top portion 109 of body 102. As shown in FIG. 1b, sensor apertures 112a, 112b each include a bore portion 114a, 114b and a counterbore portion 116a, 116b, though embodiments without a counterbore are contemplated. It is contemplated herein that the sizes of sensor apertures 112a, 112b and associated parts can be sized to accept whatever sensor is desirable for a given sensing application.

Referring to FIG. 1b, liquid flow bore 117 is formed through body 102 substantially between entry portion 105 and exit portion 107. Although the embodiment illustrated in FIG. 1b shows liquid flow bore 117 as being substantially perpendicular to the first and second sensor apertures 112a, 112b, other relationships between the bores are contemplated. Liquid flow bore 117 comprises an ingress portion 119 adjacent entry portion 105 of body 102, a narrowed portion 120, and an egress portion 121 adjacent the exit portion 107 of body 102. In some embodiments, ingress portion 119 and egress portion 121 can have larger diameter than narrowed portion 122. Liquid stream 120a enters ingress portion 119 of liquid flow bore 117 through ingress orifice 118 formed in entry portion 105. Once liquid stream 120a has entered ingress portion 119, the liquid stream is optionally narrowed at aperture 121 and flows through narrowed portion 122. Liquid stream 120a then passes through an egress aperture 124, through egress portion 121 of liquid flow bore 117, and out of body 102 through an egress orifice 126 formed in exit portion 107. It is apparent that liquid stream 120a, which in the illustrated embodiment becomes the liquid stream flowing through narrowed portion 122 of liquid flow bore 117, may comprise industrial water of an industrial water system, a cleaning liquid, a separate water-containing liquid, or combinations thereof.

As shown in FIG. 1b, bore portions 114a, 114b of sensor apertures 112a, 112b, fluidly communicate with narrowed portion 120 of liquid flow bore 117. First and second sensor openings 115a, 115b are formed at the intersection between the respective first and second sensor apertures 112a, 112b and liquid flow bore 117. In certain embodiments, surfaces 1110a, 1110b of sensors 110a, 110b are disposed in sensor openings 115a, 115b. As a result, liquid stream 120a flowing through body 102 contacts pH sensor 110a and oxidation-reduction potential sensor 110b at surfaces 1110a and 1110b thereof.

With continued reference to FIG. 1b, gas flow bore 128 is formed in body 102 substantially parallel to liquid flow bore 117 to allow for flow of a gaseous stream 130 into the body for introduction into the liquid flow bore substantially opposite sensor apertures 112a and 112b. Gas flow orifice 128 has a gas ingress portion 129 adjacent exit portion 107 and a narrowed gas portion 131. In the embodiment shown in FIG. 1b, first and second jet channels 132a, 132b are formed in body 102 and provide fluid communication between the narrowed gas portion 131 of the gas flow bore 128 and the liquid flow bore 117. The first jet channel 132a terminates in narrowed portion 122 of liquid flow bore 117 at a first countersinked opening 2110a, and second jet channel 132b terminates in the narrowed portion of the liquid flow bore at a second countersinked opening 2110b. The first countersinked opening 2110a opens into narrowed portion 122 substantially opposite first sensor aperture 112a, and second jet channel 132b opens into the narrowed portion substantially opposite second sensor aperture 112b. Although the embodiment illustrated in FIG. 1b includes two jet channels 132a, 132b corresponding to two sensor apertures 112a, 112b, it is contemplated that different amounts of jet channels can branch from gas flow bore 128 depending on the number of sensors used in a given apparatus, or the number of sensors that a user wishes to clean via introduction of a gaseous stream.

As shown in FIG. 1b, gaseous stream 130 is introduced into gas ingress portion 129 of gas flow bore 128 at a gas ingress orifice 133 formed in exit portion 107 of body 102. Gaseous stream 130 then passes through a gas aperture 134 into narrowed gas portion 131 of gas flow bore 128. Gaseous stream 130 then splits into either the first or second jet channels 132a, 132b and is expelled through the respective first or second countersinked openings 2110a, 2110b into narrowed portion 122 of liquid stream 120, thereby creating a gaseous and liquid stream 150. For the embodiment illustrated in FIG. 1b, gaseous stream 130 is introduced in a direction perpendicular to liquid stream 120, in this instance, narrowed portion 122. As illustrated, gaseous stream 130 is introduced through two countersinked openings 2110a and 2110b, corresponding to each of the surfaces 1110a and 1110b of pH sensor 110a and oxidation-reduction potential sensor 110b. Though optional, countersinked openings 2110a and 2110b of the embodiment illustrated in FIG. 1b are tapered to provide distribution across wetted surfaces 1110a and 1110b of pH sensor 110a and oxidation-reduction potential sensor 110b. In other embodiments, such as the embodiment shown in FIG. 1d, jet channels 132a, 132b terminate into narrowed portion 122 at first and second nozzles 3110a, 3110b. In such embodiments, gaseous stream 130 enters narrowed portion 117 through nozzles 3110a, 3110b that are not countersunk. As a result, gaseous stream 130 mixes with the liquid stream 120 as a more direct jet than when the countersinked openings 2110a, 2110b are used. In some embodiments, openings of first and second nozzles 3110a, 3110b have a substantially smaller diameter than the respective first and second jet channels 132a, 132b. As is evident from the embodiment illustrated in FIG. 1b, gaseous stream 130 may be configured to operably supply a gaseous substance to a single surface, a plurality of gaseous substances to a plurality of surfaces, a single gaseous substance to a plurality of surfaces, or however the user sees fit, using valves, conduits, fittings, and the like.

In certain embodiments, the liquid stream comprises, or may consist of or consist essentially of, water. In a preferred embodiment, the liquid stream is an industrial water stream from an industrial water process. In other embodiments, the liquid stream may be a liquid cleaning chemical. In some embodiments, the surface is isolated as described herein and the combined gaseous and liquid stream is contacted with the surface. In some embodiments, the liquid stream contacts the surface during isolation via circulation (e.g., recirculation), where the liquid stream may comprise industrial water from the industrial water process.

In certain embodiments, a liquid stream is contacted with a surface utilized for measuring a parameter with a sensor. The surface may be connected to the sensor in the form of a wetted surface of the sensor itself, i.e., a sensing component of the sensor. The surface may be a wetted surface of a light transference medium.

In certain embodiments, the liquid stream is contacted with a corrosion coupon, which is removed and observed to evaluate for general and local corrosion. When present, the corrosion coupon is exposed to the liquid stream generally following a standardized protocol, e.g., an ASTM standard. The coupon can be removed from the liquid stream in order to measure e.g., weight loss or depth of pitting, when present.

In certain embodiments, the gaseous stream is introduced into the liquid stream, which may be an industrial water stream, at a gaseous pressure of from about 10 psi to about 100 psi greater than the liquid stream pressure. The term "gaseous stream" refers to flow of a gas-phase substance. An exemplary embodiment of a gaseous stream is a stream of compressed air. The gaseous stream pressure may be at least about 10 psi greater than the liquid stream pressure, or about 20 psi greater than the liquid stream pressure, and up to about 100 psi greater than the liquid stream pressure, or up to about 80 psi greater than the liquid stream pressure, or up to about 60 psi greater than the liquid stream pressure, or up to about 40 psi greater than the liquid stream pressure. In a preferred embodiment, the gaseous stream is introduced into the liquid stream at a gaseous pressure of from about 20 psi to about 40 psi greater than the liquid stream pressure.

In certain embodiments, the surface is located in a narrowed portion of the liquid stream, which may be an industrial water stream. In a preferred embodiment, the surface located in a narrowed portion of the liquid stream is at least one of a wetted surface of a pH sensor and a wetted surface of an oxidation-reduction potential sensor. The flow of the liquid stream becomes narrowed just upstream from the surface, and then a gaseous stream is introduced into the narrowed portion so as to create a combined gaseous and liquid stream, which thereby contacts the surface. The narrowing of the liquid stream has been demonstrated to provide particularly beneficial results when used in combination with the introduction of the gaseous stream at a gaseous stream pressure of from about 10 psi to about 100 psi greater than the liquid stream pressure. Evidence of the aforementioned beneficial results is demonstrated, e.g., in the Examples provided herein.

In certain embodiments, the gaseous stream is introduced into the liquid stream toward the surface utilized in measurement of a parameter of the industrial water in the industrial water system. In certain embodiments, the gaseous stream is introduced into the liquid stream in a direction perpendicular from the flow of the liquid stream. In certain embodiments, the gaseous stream is introduced into the liquid stream at an angle ranging from about ±45 degrees from a direction perpendicular from the flow of the liquid stream. In certain embodiments, the gaseous stream is introduced into the liquid stream at a location upstream of the surface utilized in measurement of a parameter of the industrial water. In certain embodiments, the gaseous stream is introduced in the direction of flow of the liquid stream. In certain embodiments, the gaseous stream is introduced into the liquid stream such that the liquid stream flowing across the surface utilized in measurement of a parameter of the industrial water in the industrial water system is unimpeded by a gaseous stream delivery vessel. For example, as illustrated in FIG. 1b, gaseous stream 130 is delivered into liquid stream 120 without placing delivery equipment, or equipment of any kind, into the flow of liquid stream 120.

The gaseous stream of the embodiments described herein may comprise any one or more of several gaseous substances. The gaseous stream may comprise gaseous substances ranging from alkaline to inert to acidic. In certain embodiments, the gaseous stream comprises a gaseous substance selected from the group consisting of air, nitrogen, oxygen, an acid gas, an alkaline gas (e.g., gaseous ammonia), and combinations thereof, with the caveat that the acid gas and the alkaline gas are not in combination.

The term "acid gas" refers to a gaseous substance that, if combined with (e.g., dissolved in) water, turns the water acidic. Exemplary embodiments of acid gases include certain carbon-containing gases, sulfur-containing gases, nitrogen-containing gases, and chlorine-containing gases. An exemplary embodiment of a carbon-containing acid gas is carbon dioxide. An exemplary embodiment of a sulfur-containing acid gas is sulfur dioxide. An exemplary embodiment of a nitrogen-containing acid gas is nitrogen dioxide. An exemplary embodiment of a chlorine-containing acid gas is chlorine.

Acid gases that may be utilized to practice the inventive methods include, but are not limited to, a carbon-containing acid gas, a sulfur-containing acid gas, a nitrogen-containing acid gas, a chlorine-containing acid gas, and combinations thereof. An embodiment of a carbon-containing acid gas is carbon dioxide. An embodiment of a sulfur-containing acid gas is sulfur dioxide. An embodiment of a nitrogen-containing acid gas is nitrogen dioxide and precursors thereof. An embodiment of a chlorine-containing acid gas includes chlorine.

Not wishing to be bound by theory, it is believed that the introduction of a gaseous stream into the liquid stream transfers mechanical energy to the surface utilized for measuring a parameter, thereby tending to physically (as opposed to chemically) remove or inhibit deposition. Should the gaseous stream tend to be acidic, the removal or inhibition of deposition is believed to be accomplished via physical and chemical action associated with introduction of the acid gas, which is believed to hold true for an alkaline gaseous stream as well.

In certain embodiments, pellets of carbon dioxide are introduced with the gaseous stream into the liquid stream, which may be an industrial water stream. The phrase "pellets of carbon dioxide" refers to solid pellets comprising carbon dioxide and possibly other substances. Carbon dioxide pellets of the present disclosure are available from Allteq Industries, Inc., 355 Lindbergh Ave., Livermore, Calif., and Kyodo International, Inc., 9-10-9 Miyazaki, Miyamae-ku, Kawasaki-shi, Kanagawa-ken, 216-0033, Japan. The pellets may be generally spherical. In certain embodiments, the pellets have a diameter of from about 0.1 μm to about 0.3 mm, including from about 0.1 μm, or about 1 μm, or from about 10 μm, to about 0.1 mm, or to about 0.2 mm, or to about 0.3 mm.

Figure 1D:
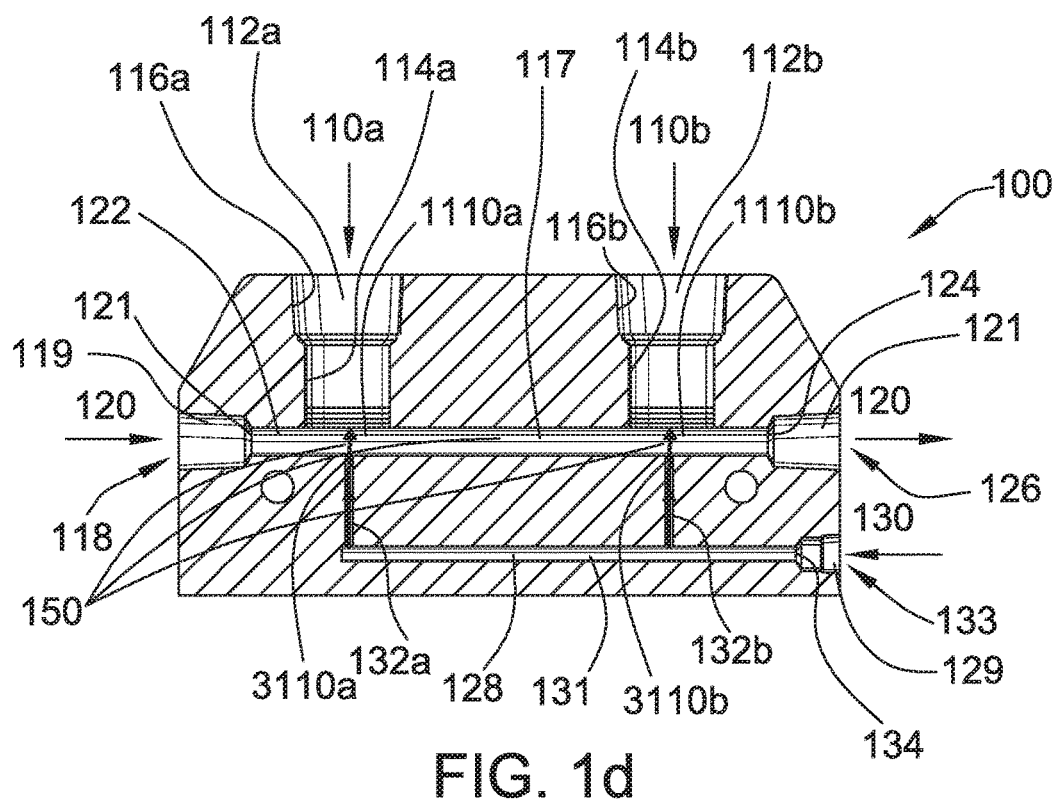
FIG. 1d illustrates an embodiment of an apparatus that may be used to perform methods of the present disclosure.

As shown in FIG. 1d, gaseous stream 130, which would include the pellets of carbon dioxide, can be fed pneumatically into the liquid stream through nozzles 3110a and/or 3110b, which replace countersinked openings 2110a and/or 2110b when implemented. The pellets may be introduced into the gaseous stream along with any of the gaseous substances disclosed herein. Preferred gases to utilize in delivery of the carbon dioxide pellets include, e.g., at least one of air and gaseous carbon dioxide.

Figure 1E:
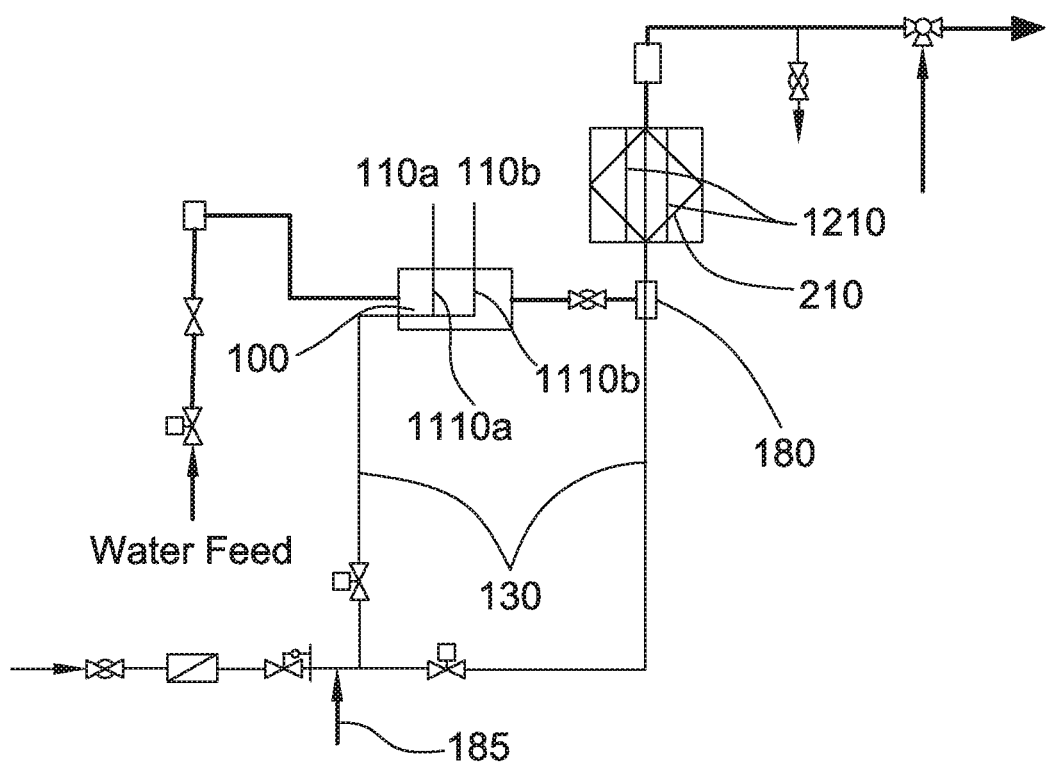
FIG. 1e illustrates a plan view of an embodiment of a system that may be used for performing methods of the present disclosure.

FIG. 1e illustrates an embodiment of a system that may be utilized to perform the introduction of the carbon dioxide pellets into gaseous stream(s) 130, e.g., via stream 185. A person of skill in the art will recognize that stream 185 should be configured to provide effective feed of the carbon dioxide pellets such that the resulting combined gaseous stream 130 provides adequate contact to any or all of surfaces 1110.

Any surface critical to the measurement of one or more parameters of industrial water utilized in an industrial water system is contemplated by the methods of the present disclosure. The phrase "industrial water utilized in an industrial water system" is intended to include industrial water that is, has been, or will be used in an industrial water system. As it is commonly used, the term "stream" denotes fluid flow, generally through a conduit (e.g., a pipe).

By way of example, sensors that may be utilized in measuring parameters of industrial water in an industrial water system include, but are not limited to, a temperature sensor, a pH sensor, an oxidation-reduction potential sensor, a corrosion detection sensor, an optical sensor, a weight-measuring sensor, and a flow meter. Multiple sensors may be utilized for monitoring and optionally controlling an industrial water system, which may include multiple sensors of a single type of sensor (e.g., two fluorometers), multiple types of sensors (e.g., a pH sensor, an oxidation-reduction potential sensor, and a fluorometer), and combinations thereof (e.g., two fluorometers, a pH sensor, and three oxidation-reduction potential sensors).

Reference to the term "optical sensor" is made to denote a device that at least in part relies on light transmission and detection to determine a parameter associated with a substance. For example, a fluorometer may determine the concentration of a chemical species in a liquid by transmitting light at an excitation wavelength into the liquid, and detecting light at an emission wavelength out of the liquid. Depending on the application and substance, optical sensors may measure, for example, fluorescence, absorption, temperature, chemiluminescence, optical scattering (e.g., Rayleigh, Mie, and Raman scatter), imaging, transmittance, particle size, particle count, and turbidity.

At a minimum, an optical sensor is capable of receiving an optical signal to detect a parameter of a substance. The optical sensor may also send an optical signal that may be used to generate the optical signal received by the optical sensor. If an optical signal is generated, it is typically directed to a particular location. An optical signal may, for example, be directed to shine through a light transference medium and into a liquid (e.g., an industrial water stream) in order to perform an optical measurement of a parameter of the liquid using the same or a different optical sensor. Reference to the term "optical measurement" denotes using light to determine a parameter of a substance using an optical sensor.

By way of example, embodiments of an optical sensor include, but are not limited to, a fluorometer, a spectrophotometer, a colorimeter, a refractometer, a luminometer, a turbidimeter, and a particle counter. Multiple optical sensors may be utilized for monitoring and optionally controlling an industrial water system, which may include multiple optical sensors of a single type of optical sensor (e.g., more than one fluorometer), multiple types of sensors (e.g., a fluorometer and a colorimeter), and combinations thereof (e.g., two fluorometers, a spectrophotometer, and three refractometers). Generally, the surface critical to the measurement of one or more parameters using an optical sensor is a wetted surface of a light transference medium.

By way of example, embodiments of surfaces critical to the measurement of one or more parameters of industrial water in an industrial water system include, but are not limited to, a wetted surface of a temperature sensor, a wetted surface of a pH sensor, a wetted surface of an oxidation-reduction potential sensor, a wetted surface of a corrosion detection sensor, a wetted surface of a light transference medium, a wetted surface of a corrosion coupon, a wetted surface of a flow meter, and combinations thereof.

A light transference medium allows light to transfer through itself, or, if appropriate, reflect from itself, so that the light may be used to perform an optical measurement of a parameter of a substance using an optical sensor. Preferably, light transference media are used for optical transference, and hence are preferably transparent as defined in ASTM D1746. However, depending on the particular application, complete transparency of a light transference medium may not be necessary. Examples of light transference media include a flow cell, an optical window, a reflective surface, a refractive surface, a dispersive element, a filtering element, and an optical fiber sensor head. Prevention or removal of deposition on a wetted surface of a light transference medium should lead to greater transparency or, in some embodiments, light reflectance, of the light transference medium, which should lead to more accurate measurements via an optical sensor.

As suggested by the previous paragraph, in some embodiments, a light transference medium comprises a surface utilized to reflect light. The light may partially or totally reflect from the reflective surface of the light transference medium.

In certain embodiments utilizing a flow cell as a light transference medium, the method further comprises fanning the combined gaseous and industrial water stream as it flows toward the wetted surface of the light transference medium. While not wishing to be bound by theory, the fanning is performed so as to provide better inhibition and/or removal of deposition on the wetted surface of the flow cell by forcing the gas of the combined gaseous and industrial water stream to come in better contact with the wetted surface of the light transference medium.

Figure 2:
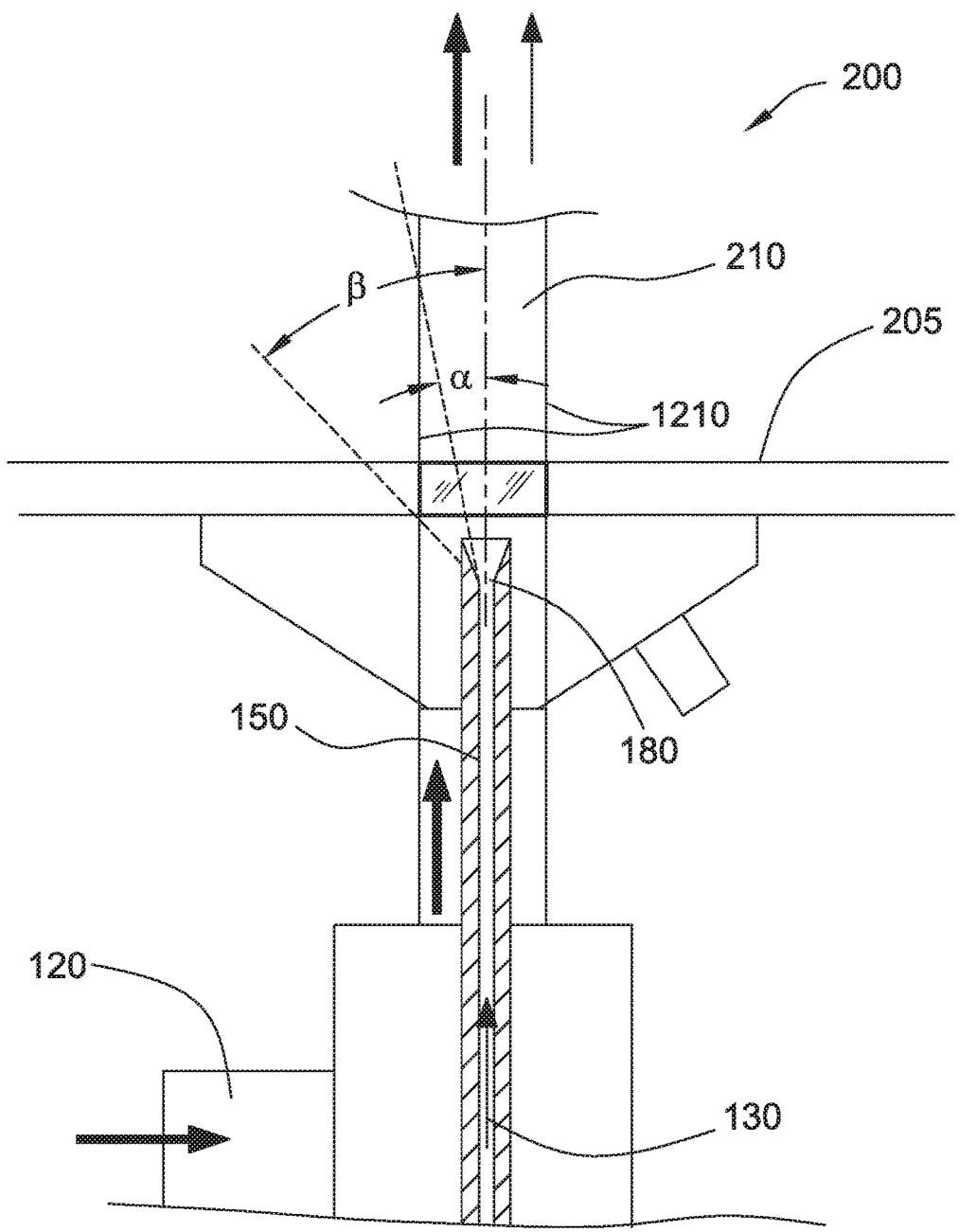
FIG. 2 illustrates a plan view of an embodiment of a system that may be used for performing methods of the present disclosure.

FIG. 2 illustrates an embodiment of a system 200 for performing methods of the present disclosure, wherein the system 200 incorporates a optical sensor 205 coupled with a flow cell 210, an exemplary embodiment of a light transference medium, having a wetted surface 1210. As illustrated, a liquid stream 120 flows through flow cell 210. Upstream from flow cell 210, gaseous stream 130 is introduced into liquid stream 120. The combined gaseous and liquid stream 150 flows so as to contact the wetted surface 1210 of the flow cell 210.

The contacting may be enhanced via nozzle 180, which may be configured so as to provide further turbulence through the flow cell 210. Nozzle 180 may be constructed and positioned so as to provide varying degrees of fanning ($\alpha$, $\beta$) toward the wetted surface 1210 of flow cell 210.

In certain embodiments, the gaseous stream is introduced intermittently into the industrial water stream. The terms "intermittent" and "intermittently" are utilized herein to describe the practice of performing a method or step thereof, ceasing performance of the method or step thereof, and later repeating performance of the method or step thereof, without regard to the timing of the performance. In certain embodiments of the illustrative embodiments, the gaseous stream is introduced intermittently at pre-determined time intervals.

In certain embodiments, the gaseous stream is introduced on an as-needed basis as determined via, e.g., measurement data trends. For example, a consistent increase or decrease in measurement of a variable over time, even if slight, may indicate the need to introduce the gaseous stream into the industrial water stream. An example of a consistent increase or decrease could be illustrated by, e.g., a consistent change (i.e., change in one direction) of ±about 1% to about 10% of a value over a period of time of, e.g., about 1 hour, when the sample water is known to be approximately the same composition (e.g., no spikes in contamination) and at conditions (temperature, pressure, etc.) that are approximately unchanging. A consistent change in a measured variable can indicate obstruction (e.g., fouling) across the surface. After performing a method as described herein, post-cleaning measurements utilizing the surface can be compared to determine whether obstruction of the surface is causing the variability, or whether the sensor performing the measurements is failing, which is further described herein.

A method of operating a cooling water system is also provided. The method comprises contacting a cooling water stream at a cooling water stream pressure with a surface utilized for measuring a parameter with a sensor. A gaseous stream is introduced into the cooling water stream, thereby causing the combined gaseous and cooling water stream to contact the surface. The gaseous stream introduced at a gaseous stream pressure of from about 10 psi to about 100 psi greater than the cooling water stream pressure. Introduction of the gaseous stream causes the combined gaseous and cooling water stream to contact the surface.

In certain embodiments, the surface utilized in measurement of a parameter of the industrial water system is located in a narrowed portion of the liquid stream.

Figure 3:
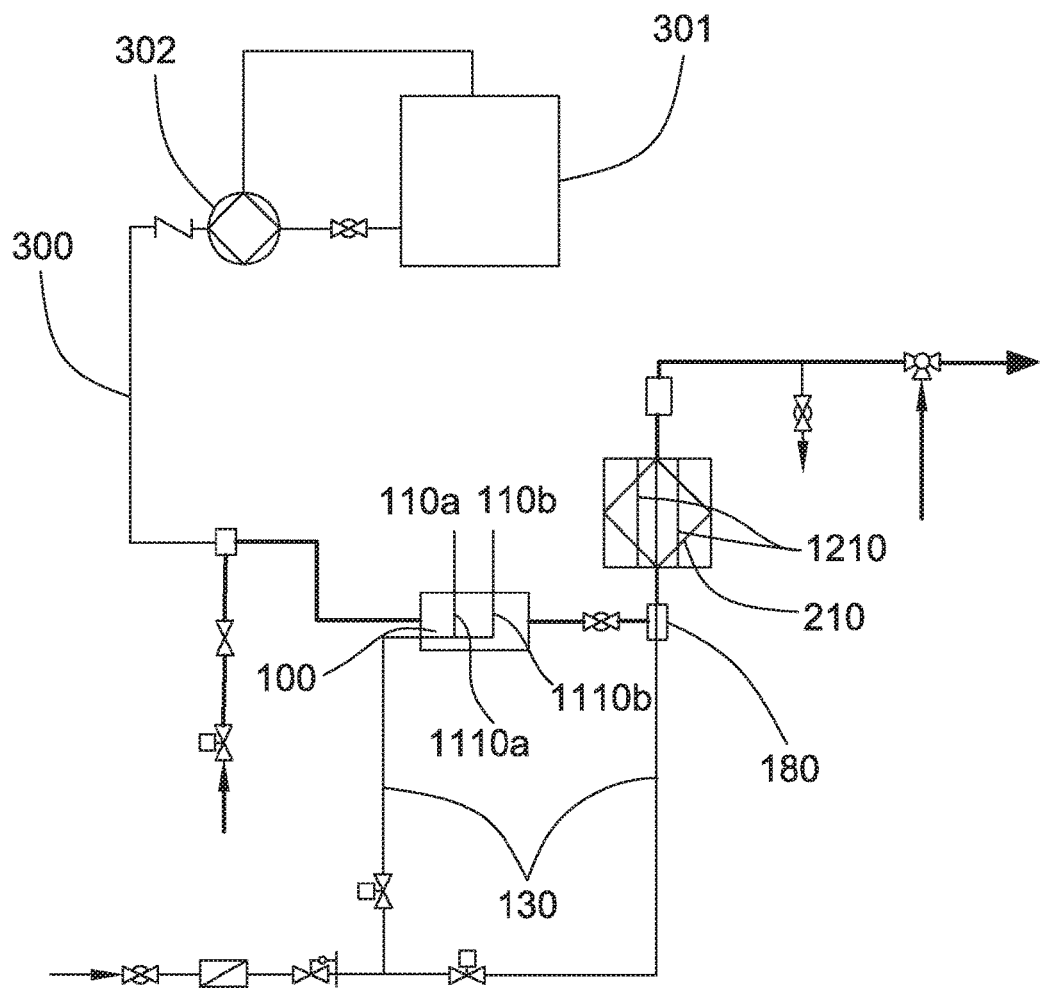
FIG. 3 illustrates a plan view of an embodiment of a system that may be used for performing methods of the present disclosure.

As discussed herein, in certain embodiments, the liquid stream comprises a cleaning solution. FIG. 3 shows an embodiment of a system that incorporates aspects of the embodiments illustrated in FIGS. 1a, 1b, and 2, and further comprises a system for administering a cleaning solution into the wetted portions of the system. A person skilled in the art will recognize that the embodiments of FIGS. 1c and 1e, though omitted from FIG. 3, can be implemented into the embodiment of FIG. 3. Furthermore, the skilled artisan will recognize that FIG. 3 shows an embodiment of the isolated first subset of sensors as described in the method that utilizes a plurality of parameters, further described herein.

In the embodiment of FIG. 3, a cleaning solution is supplied to the wetted surfaces 1110a, 1110b, and 1210, of pH sensor 110a, oxidation-reduction potential sensor 110b, and flow cell 210, via a cleaning solution supply tank 301 and a cleaning solution pump 302. A person skilled in the art will recognize that the cleaning solution supply tank 301 and the cleaning solution pump 302 are merely illustrative embodiments of apparatuses that may be utilized to provide a cleaning solution to the wetted surfaces 1110a, 1110b, and 1210.

In certain embodiments, the cleaning solution is an aqueous cleaning solution. In some embodiments, the cleaning solution comprises water and an ingredient selected from the group consisting of: a urea salt, a mineral acid, an organic acid, a peroxyacid, a detergent, an emulsifier, and combinations thereof. A person of ordinary skill in the art will recognize that certain chemical species will fit the description of more than one of the aforestated ingredients.

Exemplary urea salts include, but are not limited to, urea hydrogen chloride, urea hydrogen sulfate, urea hydrogen nitrate, and urea hydrogen phosphate. Exemplary mineral acids include, but are not limited to, hydrochloric acid, nitric acid, sulfuric acid, phosphoric acid, and boric acid. Exemplary organic acids include, but are not limited to, carboxylic acid, acetic acid, peracetic acid, citric acid, and oxalic acid. In some embodiments, the cleaning solution comprises water and an ingredient selected from the group consisting of: urea hydrogen chloride, phosphoric acid, sulfuric acid, nitric acid, a peroxyacid, a detergent, an emulsifier, and combinations thereof. In a preferred embodiment, the aqueous cleaning solution comprises water and urea hydrogen chloride.

In certain embodiments, the aqueous cleaning solution (i.e., a cleaning solution comprising water) has a solids concentration of from about 1 weight percent solids to about 99 weight percent solids, including from about 1 weight percent solids, or about 10 weight percent solids, or from about 20 weight percent solids, or from about 30 weight percent solids, to about 40 weight percent solids, or to about 60 weight percent solids, or to about 90 weight percent solids, or to about 99 weight percent solids. The phrase "weight percent solids" is used to denote the percent by weight of the aqueous cleaning solution that is made up of one or more ingredients other than water. In a preferred embodiment, the aqueous cleaning solution comprises water and urea hydrogen chloride, wherein the urea hydrogen chloride is present in the aqueous cleaning solution at a concentration of from about 10 weight percent to about 90 weight percent, including from about 10 weight percent, or from about 20 weight percent, or from about 30 weight percent, to about 60 weight percent, or to about 80 weight percent, or to about 90 weight percent.

Exemplary embodiments of peroxyacids include, but are not limited to, peracetic acid, peroxtanoic acid, and combinations thereof.

Exemplary embodiments of detergents include, but are not limited to, diethylene glycol, polyoxyethylene stearate, tridodecylmethylammonium chloride, sodium dodecylsulfate, dihexadecyl phosphate, octylphenylpolyethylene glycol (e.g., compositions of CAS No. 9002-93-1), and combinations thereof.

An exemplary embodiment of an emulsifier includes, but is not limited to, sodium xylene sulfonate.

In a particularly preferred embodiment, the method chemically cleans at least one of a wetted surface of a pH sensor and a wetted surface of an oxidation-reduction potential sensor utilizing aqueous urea hydrogen chloride, and the responsiveness of the utilized pH sensor and/or oxidation-reduction potential sensor is monitored by comparing historical data gathered during previous chemical cleaning cycles. Generally, as pH and oxidation-reduction potential sensors age, a decomposition process occurs in their respective sensing components, thereby changing the chemical composition of membranes utilized in each. Average lifetime for a pH or oxidation-reduction potential sensor is application dependent and can range from a few weeks to greater than a year. Assuming that the industrial water system is in operation for an extended period of time, the pH sensor and/or oxidation-reduction potential sensor will need to be replaced.

The decomposition process results in the thickening of a hydrated gel layer, which makes up the sensing component of a pH sensor and an oxidation-reduction potential sensor. Thickening of the hydrated gel layer causes less dynamic change in the hydrated gel layer, which can lead to inaccurate measurement of the respective parameters. Damage or degradation of the hydrated gel layer can occur due to numerous sources, such as, e.g., exposure to high acidic or alkaline chemistry, mechanical cleaning, high temperature, deposition, etc. As a result, the response time for the probe becomes slower and calibration must be done more frequently than for less utilized sensors.

Measuring response times of pH sensors and oxidation-reduction potential sensors has generally been limited to data collection during calibration procedures that involve removing the sensors and placing them in a known standard solution. Using the chemical cleaning method of the present disclosure, response time can be compared against previously collected data to assess sensor degradation. In embodiments utilizing multiple sensors of the same type, a comparison against redundant sensors exposed to the same process stream and cleaning solution can also provide information related to the response times of each sensor. A slow response or measurement offset from one sensor compared against another would be an indication of degradation.

In a preferred embodiment, the method utilizes chemical cleaning with aqueous urea hydrogen chloride and further comprises isolating a first subset of surfaces from an industrial water stream, wherein the first subset of surfaces comprises a wetted surface of a pH sensor and a wetted surface of an oxidation-reduction potential sensor. The first subset of surfaces is cleaned by contacting it with an aqueous urea hydrogen chloride cleaning solution for a period of time sufficient to return the pH sensor and the oxidation-reduction potential sensor to an acceptable level, which can be determined based on, e.g., a previous calibration and/or measurements taken following the re-establishment of contact of the liquid stream to the surface utilized in measurement. The pH signal decreases and the oxidation-reduction potential signal increases because urea hydrogen chloride is both an acid and an oxidizer.

The cleaning solution may contact the wetted surfaces of the isolated subset, which may include a light transference medium. In an embodiment, the chemical solution may flow through the isolated subset for about 3 minutes at a rate of about 3 gallons per day. In certain embodiments, once filled, the cleaning solution contacts the wetted surfaces without flowing for a period of time. In other embodiments, the cleaning solution is immediately flushed from the wetted surfaces upon acceptable cleaning, which may be done using industrial water from the industrial water system.

When industrial water flow is re-initiated, the pH and oxidation-reduction potential signals return back to industrial water conditions following a double exponential decay for oxidation-reduction potential sensors, and growth for pH sensors. The characteristic time parameters calculated from the double exponential analysis give insight into the decomposition, or lack thereof, in the oxidation-reduction potential sensor and/or pH sensor. Historically tracking selected parameters over time, the oxidation-reduction potential sensor (and a corresponding pH sensor, if utilized) can be monitored or replaced as needed. In certain embodiments of the illustrative embodiments, the oxidation-reduction potential sensor is replaced periodically, for example, every 4-8 months. In certain embodiments of the illustrative embodiments, the pH sensor is replaced periodically, for example, every 4-8 months.

When used, a pH sensor may show signs of sporadic measurement variation or sluggish response time during calibration, either of which suggests that deposition may be occurring on the wetted surface of the pH sensor. Either phenomenon may cause the affected pH sensor to fail calibration.

Data showing the dynamic behavior of an oxidation-reduction potential sensor after exposure to aqueous urea hydrogen chloride is shown in Table 1. Exemplary features of the oxidation-reduction potential sensor's signal behavior are labeled in Table 1. Response time after exposing the oxidation-reduction potential sensor to industrial water of an industrial water system shows a characteristic two-phase model to account for the fast and slow response behavior given by Formula 1:

$$ORP(t) = Ae^{-\tau_f t} + Be^{-\tau_s t} + \text{Offset} \qquad (1)$$

wherein A is constant for the fast response term, $\tau_f$ is the fast time constant, B constant for the slow response term, $\tau_s$, is the slow time constant, and the Offset is the approximate oxidation-reduction potential sensor signal just prior to the sensor contacting the aqueous urea hydrogen chloride (an example of a cleaning solution). After exposing the oxidation-reduction potential sensor to aqueous urea hydrogen chloride, the sensor response increases due to oxidation caused by the aqueous urea hydrogen chloride. At time t=0 after the industrial water stream begins to contact the cleaned surface, the sum of the constants A, B and Offset equals the sensor signal level. The signal level tends to decay following the sum of the terms in Formula 1, wherein the critical parameters associated with the sensor response behavior are the time constants $\tau_f$ and $\tau_s$. The reciprocal of the time constants allows for the estimation of the decay time to reach the Offset. In particular, an increase in the value of $1/\tau_s$ for a sensor indicates that the sensor's response is degrading.

In a further aspect, the method comprises contacting an industrial water stream at an industrial water stream pressure with at least one of a wetted surface of a pH sensor and a wetted surface of an oxidation-reduction potential sensor. The pH and/or oxidation-reduction potential of the industrial water stream is measured. A cleaning solution comprising urea hydrogen chloride is contacted with at least one of the wetted surfaces for a first period of time and at a concentration sufficient to clean the at least one of the wetted surfaces. The industrial water stream is re-contacted with the cleaned at least one of the wetted surfaces at the industrial water stream pressure for a second period of time, thereby measuring pH and/or oxidation-reduction potential of the industrial water stream using cleaned pH and/or oxidation-reduction potential sensors. A recovery curve is created that is related to the measured pH and/or the measured oxidation-reduction potential using the cleaned pH and/or oxidation-reduction potential sensors. The aforementioned steps are repeated. The respective recovery curves are compared (and ideally would overlap each other). If the comparison of the respective recovery curves demonstrates acceptable sensor degradation, the respective sensor may remain in service. However, if the respective sensor demonstrates unacceptable sensor degradation, the respective sensor is removed from service.

Figure 4:
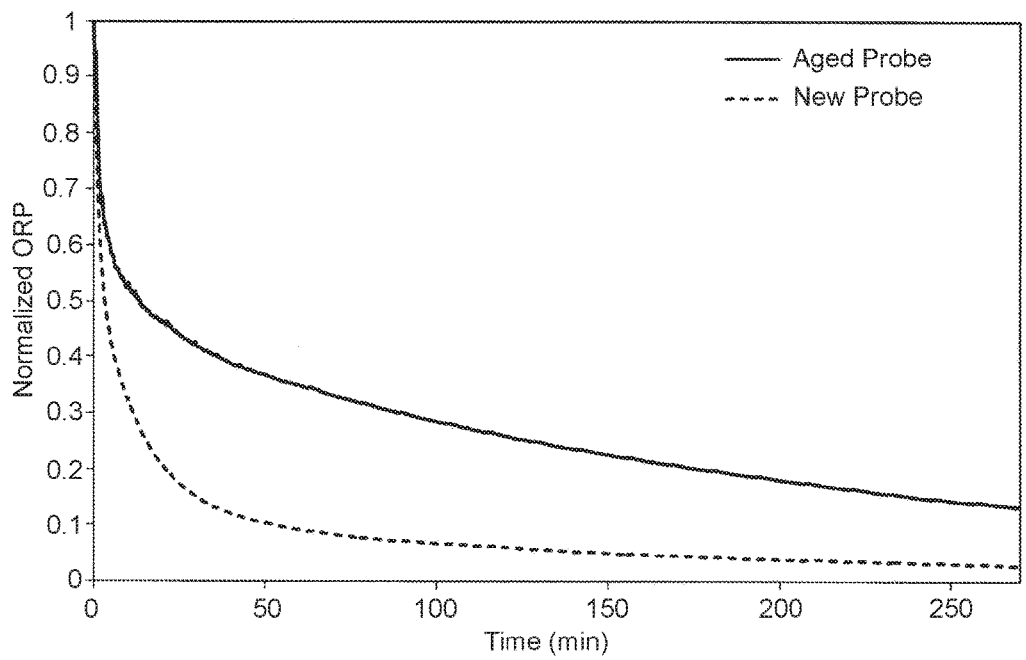
FIG. 4 illustrates oxidation-reduction potential measurement utilizing two oxidation-reduction sensor probes after chemical cleaning and exposed to a single industrial water stream.

For example, FIG. 4 illustrates recovery curves related to two different sensors and allows for the comparison of the oxidation-reduction potential sensor response for an aged sensor probe (greater than 4 months of service) and a new sensor probe exposed to the same water and a urea hydrogen chloride cleaning step. The cleaning step involved exposure of the sensing surface of the sensor probe to urea hydrogen chloride for 3 minutes at a rate of 10 gallons per day and a concentration of 60 weight percent solids, followed by 2 minutes of industrial water flow at 2 gallons per minute. FIG. 4 shoes the normalized signal response from each sensor probe at the end of the cleaning process. From FIG. 4, the response time for the aged sensor is longer compared to the new one. Quantitative analysis of the sensor response time is obtained by fitting the data to Formula 1 to determine the fast and slow time constants. The parameters for Formula 1 can be calculated and stored for historical tracking, which has been done in Table 1 below.

TABLE 1

Exemplary response time parameters for an oxidation-reduction potential sensor that utilizes a two-phase model.

| Contact time (min) | Δ Peak (mV) | FWHM (min) | $1/\tau_f$ (min) | $1/\tau_s$ (min) | A (mV) | B (mV) | Offset (mV) |
|---|---|---|---|---|---|---|---|
| 0 | 145 | 13 | 10.1 | 10.1 | 113.7 | 20.7 | 402.4 |
| 47 | 75 | 16 | 8.3 | 180.5 | 68.8 | 60.2 | 378.6 |
| 274 | 105 | 20 | 8.0 | 28.3 | 38.9 | 43.2 | 413.7 |
| 385 | 97 | 19 | 13.9 | 64.5 | 77.7 | 25.8 | 412.6 |
| 1467 | 126 | 14 | 7.8 | 94.5 | 102.7 | 34.6 | 393.3 |
| 1721 | 126 | 17 | 10.0 | 88.9 | 102.3 | 34.9 | 396.5 |
| 1952 | 122 | 20 | 9.8 | 117.2 | 88.8 | 39.0 | 400.3 |

The mathematical relationship of Formula 1 can be applied to model the responsivity of a pH sensor as well, according to Formula 2 shown below.

$$1/\text{pH}(t) = Ae^{-\tau_f t} + Be^{-\tau_s t} + \text{Offset} \qquad (2)$$

Figure 5:
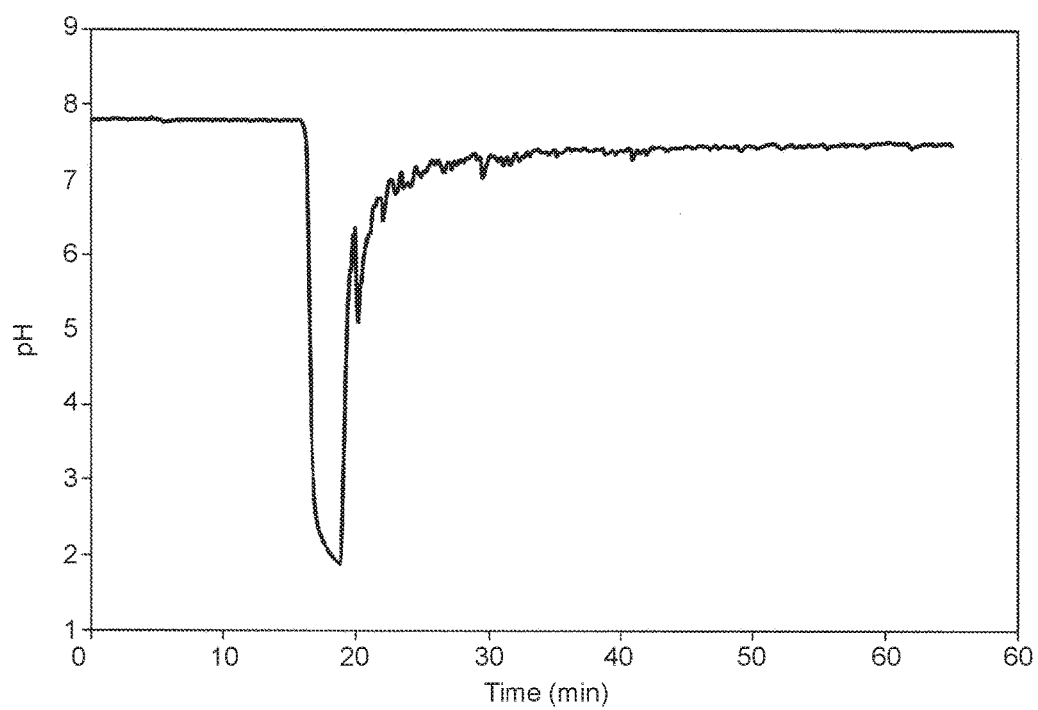
FIG. 5 illustrates pH measurement utilizing a pH sensor probe after chemical cleaning and exposed to an industrial water stream.

As can be seen from Formula 2, the pH sensor signal follows a growth response since exposure to urea hydrogen chloride causes a decrease in pH, followed by an increase when exposed to industrial water flow. A typical pH sensor response curve resulting from a urea hydrogen chloride cleaning process as described above is shown in FIG. 5. The time constants of a pH sensor probe are determined in the manner described for the oxidation-reduction potential sensor probe, except for taking into account that the pH sensor response is the reciprocal.

In certain embodiments, unacceptable sensor degradation is determined by a deviation in measured pH and/or oxidation-reduction potential of at least about 5% at an equivalent point in time subsequent the re-contacting the sensor with the industrial water stream. In certain embodiments, unacceptable sensor degradation is determined by a deviation in measured pH and/or oxidation-reduction potential of at least about 10% at an equivalent point in time subsequent the re-contacting the sensor with the industrial water stream. In certain embodiments, the equivalent point in time subsequent the re-contacting of the industrial water stream is a point in time from about 1 minute to about 120 minutes subsequent the re-contacting of the industrial water stream. In certain embodiments, the equivalent point in time subsequent the re-contacting of the industrial water stream is a point in time from about 10 minutes to about 60 minutes subsequent the re-contacting of the industrial water stream. For example, in FIG. 4, a comparison of measured oxidation-reduction potential at points in time 50 minutes subsequent re-contacting (e.g., the curves have been normalized) shows that the "New [ORP] Probe" measures an oxidation-reduction potential of approximately 0.1, while the "Aged [ORP] Probe," which has been in service for approximately 4 months, measures an oxidation-reduction potential of approximately 0.4, which is 400% higher than measured by the "New [ORP] Probe." Comparing the curves over the span of the experiment, the "Aged [ORP] Probe" never fully recovers and no longer provides accurate measurement of oxidation-reduction potential. While a point-in-time comparison is easily implemented, any similar comparison of the deviation of recovery curves of measured pH and/or oxidation-reduction potential between a single pH or oxidation-reduction potential sensor, or comparisons between a plurality of sensors of any single type are contemplated by the inventive method.

In an embodiment, a method of maintaining accuracy in the measurement of a parameter of industrial water utilized in an industrial water system is provided. In certain embodiments, the method accelerates recovery time of an oxidation-reduction potential sensor and/or a pH sensor. To achieve this acceleration, the method comprises contacting an industrial water stream at an industrial water stream pressure with at least one of a wetted surface of a pH sensor and a wetted surface of an oxidation-reduction potential sensor. A cleaning solution is contacted with at least one of the wetted surface of the pH sensor and the wetted surface of the oxidation-reduction potential sensor. The industrial water stream is re-contacted with at least one of the wetted surface of the pH sensor and the wetted surface of the oxidation-reduction potential sensor at the industrial water stream pressure. A gaseous stream is introduced into the industrial water stream at a gaseous stream pressure of from about 10 psi to about 100 psi greater than the industrial water stream pressure and after initiation of the re-contacting.

Figure 6:
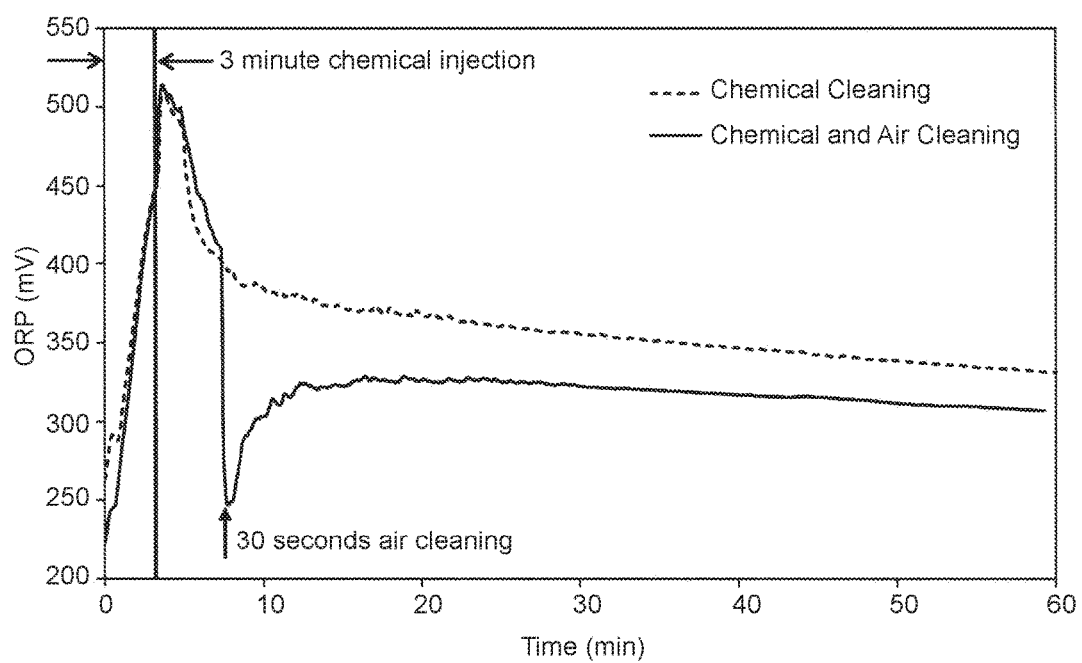
FIG. 6 illustrates oxidation-reduction potential measurement utilizing two oxidation-reduction sensor probes after chemical cleaning and exposed to a single industrial water stream, wherein one of the two probes is further exposed to a gaseous stream post-chemical cleaning.

For example, at least one of an oxidation-reduction potential sensor and a pH sensor is exposed to chemical cleaning with, e.g., urea hydrogen chloride as described herein, followed by resuming contact of the at least one sensor probe (i.e., a surface utilized in measurement of a parameter) with an industrial water stream, and then introducing a gaseous stream into the industrial water stream at a gaseous pressure of from about 10 psi to about 100 psi greater than the industrial water stream pressure. The gaseous stream may be introduced according to any of the parameters described herein related to the introduction of a gaseous stream into a liquid stream. FIG. 6 illustrates results related to the introduction of a gaseous stream post-chemical cleaning, wherein the gaseous stream is air.

In a further illustrative embodiment, the disclosure is directed to a method of maintaining accuracy in the measurement of a plurality of parameters of industrial water in an industrial water system. The method comprises contacting an industrial water stream at an industrial water stream pressure with a plurality of surfaces utilized for measuring a plurality of parameters with a plurality of sensors. A first subset of the surfaces is isolated from the industrial water stream while a second subset of the surfaces maintains contact with the industrial water stream. At least one surface of the first subset is cleaned while the second subset maintains contact with the industrial water stream. Contact with the industrial water stream is restored with the first subset of surfaces. The first subset of surfaces comprises at least one of a wetted surface of a light transference medium, a wetted surface of a pH sensor, and a wetted surface of an oxidation-reduction potential sensor. The second subset of surfaces comprises at least one of a wetted surface of a corrosion detection sensor and a wetted surface of a conductivity sensor.

An industrial water system that requires more than one surface for measuring parameters with more than one sensor is operated in a manner so that one or more surfaces that may be particularly affected by deposition can be separated from contact with the industrial water stream and cleaned. The embodiment may be implemented to allow for continued monitoring and optional control based on a subset of measured parameters of the industrial water, while another subset of parameters is not measured during in situ cleaning of its related surface(s).

In some embodiments, the term "isolating" refers to stopping the flow of the industrial water stream across the first subset of surfaces without disconnecting the industrial water system to manually clean one or more surfaces, except for, in some instances, the removal of a corrosion coupon (i.e., "system isolation"). Preferably, any data that may be generated while the first subset of sensors is isolated from the industrial water stream is not acted upon by a controller, as any such data that would be acquired during the subset's isolation would not reflect a parameter of the industrial water stream. In certain embodiments, corrosion coupons are utilized to provide data in addition to that provided by the several sensors of the embodiments disclosed herein.

In other embodiments, the term "isolating" refers to ceasing the meaningful collection of data using a sensor or subset of sensors (i.e., "control scheme isolation"). As opposed to system isolation, a sensor may be isolated if it generates data that is intentionally ignored or otherwise intentionally not acted upon by a controller. A sensor isolated in the exemplary manner may allow for the sensor to be cleaned via, e.g., introduction of a combined gaseous and liquid stream to a wetted surface thereof. The isolated sensor would not need to be isolated from the industrial water stream, but only from the control scheme. The term "meaningful data" as used herein refers to data that describes a parameter of a substance and may be input into and reliably acted upon by a control scheme.

Figure 7:
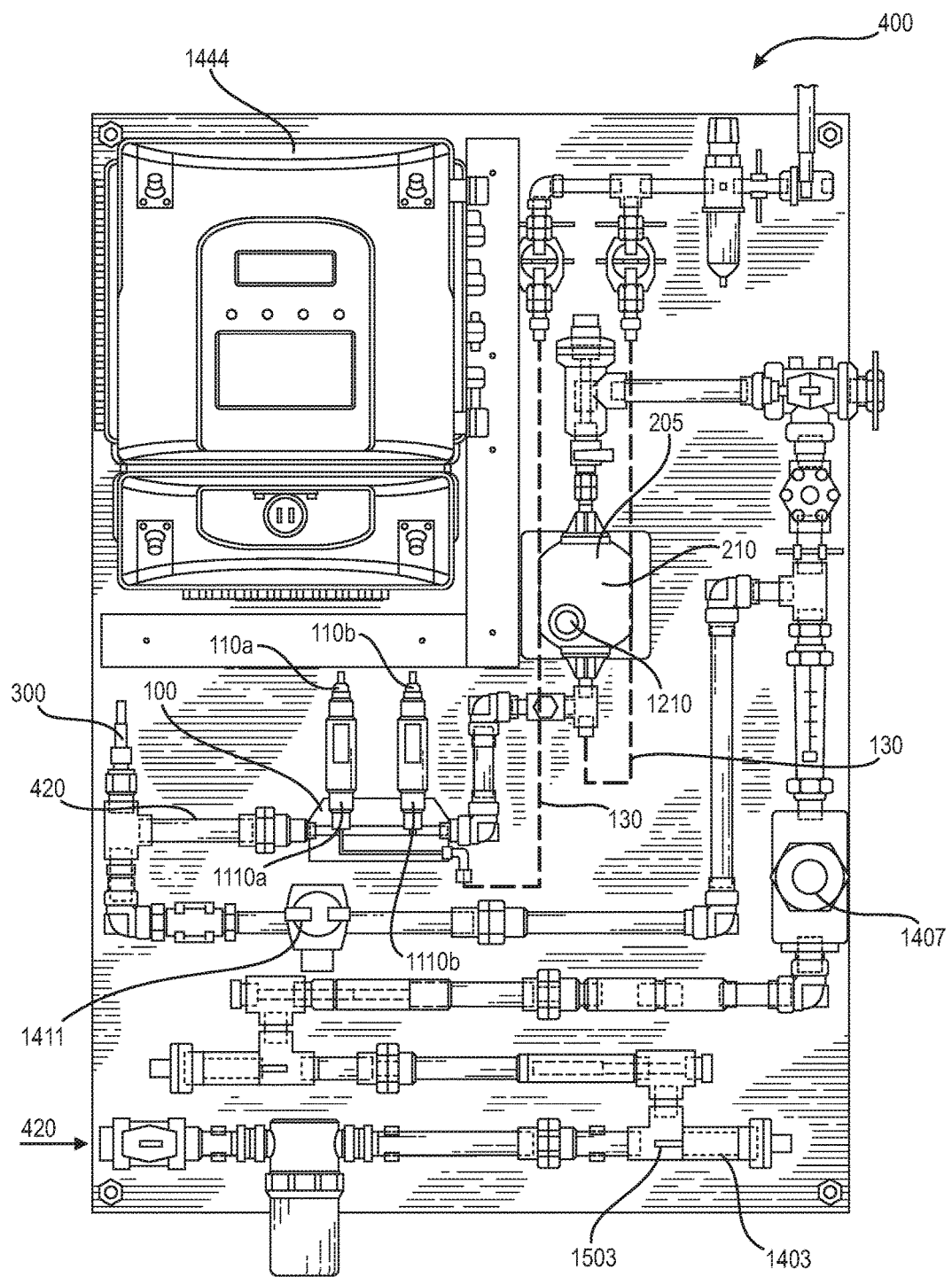
FIG. 7 illustrates a plan view of an embodiment of a system that may be used to perform methods of the present disclosure.

For example, FIG. 7 illustrates an embodiment of a system that inter alia combines several of the apparatuses and systems of the present disclosure, and may be utilized to perform any of the embodiments described herein.

FIG. 7 illustrates an embodiment of a system 400 that may be used to monitor an industrial water system, which may be a cooling water system, a heating water system, a papermaking system, a refining system, a chemical processing system, a crude oil extraction system, a natural gas extraction system, and so forth. During normal monitoring of the industrial water system using system 400, an industrial water stream 420 (corresponds to liquid stream 120 in FIGS. 1*b* and 1*d*) flows at an industrial water stream pressure through system 400 via conduits and fittings, thereby contacting a plurality of surfaces utilized for measuring a plurality of parameters of the industrial water in the industrial water system. Exemplary embodiments of the plurality of surfaces include, but are not limited to, wetted surface 1110*a* of pH sensor 110*a*, wetted surface 1110*b* of oxidation-reduction potential sensor 110*b*, wetted surface 1210 of light transference medium (e.g., flow cell) 210, wetted surface

1503 of corrosion detection sensor 1403, a wetted surface of conductivity sensor 1407, and wetted surface 1110x of fluorometer 110x (alternate embodiment of a light transference medium, shown in FIG. 1c). In the embodiment of FIG. 7, pH sensor 110a and oxidation-reduction potential sensor 110b are mounted to system 400 via apparatus 100, illustrated in FIGS. 1a, 1b, and 1d, and the light transference medium (e.g., flow cell) 210 is in operable communication with a fluorometer 205. The pH sensor 110a, the oxidation-reduction potential sensor 110b, the fluorometer 205, the corrosion detection sensor 1403, and the conductivity sensor 1407 are in communication with controller 1444, which collects and acts upon input provided by the plurality of sensors via a control scheme.

In the embodiment illustrated in FIG. 7, a first subset of the surfaces, which comprises at least one of wetted surface 1110a of pH sensor 110a, wetted surface 1110b of oxidation-reduction potential sensor 110b, wetted surface 1210 of light transference medium (e.g., flow cell) 210, and/or wetted surface 1110x of fluorometer 110x, is isolated from the industrial water stream while a second subset, which comprises at least one of wetted surface 1503 of corrosion detection sensor 1403 and a wetted surface of conductivity sensor 1407, maintains contact with the industrial water stream 420. In the embodiment, the isolation of the first subset may be a system isolation performed by actuating valve 1411 into its closed positions, or by control scheme isolation as described herein. At least one of the first subset of surfaces is cleaned while the second subset maintains contact with the industrial water stream 420, followed by restoration of contact of the industrial water stream 420 to the first subset of surfaces.

The cleaning of the first subset or a wetted surface thereof can be performed via at least one of the gaseous stream method(s) and the chemical cleaning method(s) disclosed herein. Furthermore, the isolating may be performed via at least one of system isolation and control scheme isolation, and need not be isolated in the same manner during repeated cleaning cycles. Even further, a gaseous stream may be combined with a liquid stream other than the industrial water stream (e.g., a cleaning solution stream) in order to clean the first subset or wetted surface thereof.

The following examples further illustrate the invention but, of course, should not be construed as in any way limiting its scope.

Example 1

This example demonstrates the effect of gaseous stream cleaning of an oxidation-reduction potential sensor. Two identical oxidation-reduction potential sensors were installed in a cooling water system. The cooling water system maintained a stream of cooling water having pH of from 6.5 to 7.6, conductivity of from about 1500 to about 2000 µS/cm, oxidation-reduction potential of from about 275 to about 325 mV, temperature of from 19 to 25° C., linear liquid stream speed of from about 0.68 to about 1.13 meters per second, and cooling water pressure of about 1 bar (approximately 14.5 psi). The wetted surface of Sensor A was untreated, while the wetted surface of Sensor B was treated as described herein with a gaseous stream of compressed air having a pressure of about 3 bar (approximately 43.5 psi), for 60 seconds per four hours.

Figure 8:
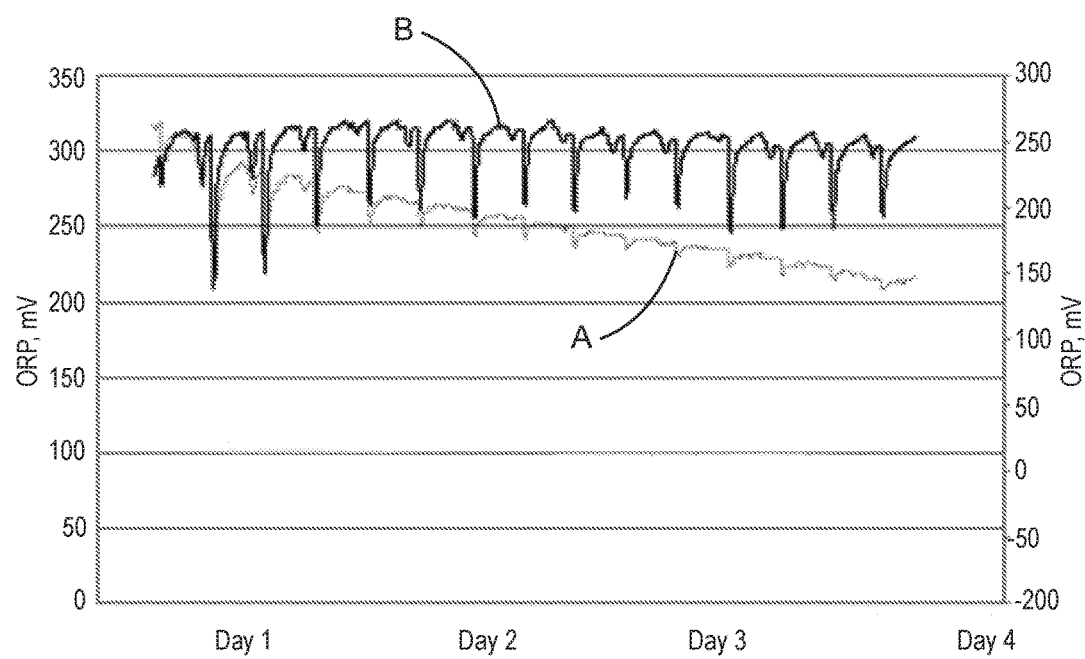
FIG. 8 is a plot of results related to Example 1 herein.

Referring to FIG. 8, for the duration of the experiment, Sensor A tended to drift from its base measurement of approximately 325 mV, while Sensor B maintained a reasonably steady base measurement. By the end of the testing period, the output of Sensor A had decreased approximately 125 mV.

Example 2

This example demonstrates the effect of chemical cleaning of an oxidation-reduction potential sensor used in an industrial water system, which in this example was a cooling water system. Two identical oxidation-reduction potential sensors were installed in a pilot cooling water system. Sensor C was installed via a tee, while Sensor D was installed via a sensor block as illustrated in FIGS. 1a and 1b. The pilot cooling water system maintained a stream of cooling water having pH of from 8.6 to 8.9, conductivity of from about 3000 to about 8500 µS/cm, oxidation-reduction potential of from about 250 to about 450 mV, temperature of from 34 to 44° C., linear liquid stream speed of from about 0.34 to about 1.03 meters per second, and cooling water pressure of about 0.4 bar (approximately 5.8 psi). The oxidation-reduction potential of the cooling water stream was verified using a calibrated Myron ULTRAMETER II™ 6 PFC$^E$ oxidation-reduction potential meter, available from MYRON L® Company, 2450 Impala Drive, Carlsbad, Calif. 92010, USA.

Figure 9:
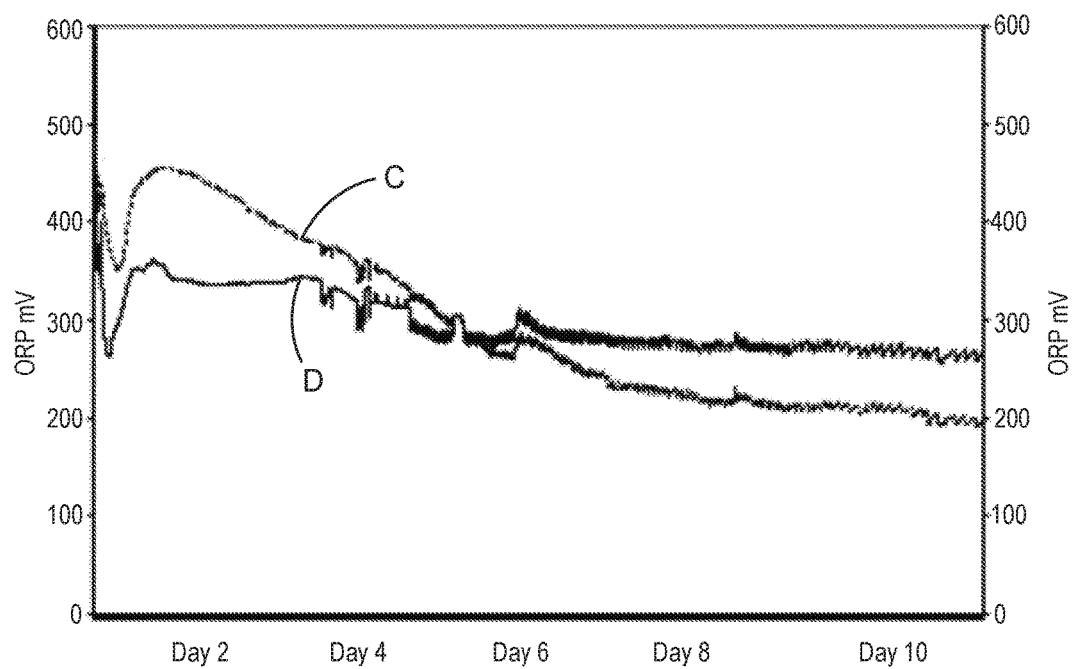
FIG. 9 is a plot of results related to Example 2 herein.

As shown in FIG. 9, at the end of the 10-day test period, Sensor D maintained a 95% output of 265 mV on average, while Sensor C erroneously measured an oxidation-reduction potential of approximately 200 mV.

Example 3

This example demonstrates the effect of chemical cleaning of a light transference medium used in an industrial water system, which in this example was a cooling water system. A wetted surface of a fluorometer flow cell used in cooling water system at a steel plant was chemically treated. Two treatment periods having differing treatment chemistries were attempted: one using an aqueous mineral acid-based cleaner comprising water, phosphoric acid, and nitric acid (e.g., TR5500 acid cleaner, comprising about 30 to about 60 weight percent phosphoric acid, about 10 to about 30 weight percent nitric acid, balance water and trace impurities, available from Nalco, an Ecolab Company, 1601 West Diehl Road, Naperville, Ill. 60563), and a second using an aqueous urea salt-based cleaner, for this example, an aqueous urea hydrogen chloride cleaner (e.g., DC14 cleaner, comprising about 30 to about 60 weight percent urea hydrogen chloride, balance water and trace impurities, available from Nalco, an Ecolab Company, 1601 West Diehl Road, Naperville, Ill. 60563). For each of the two trials, a liquid stream passed across the wetted surface of the flow cell, with the liquid stream having pH of from 7.3 to 9.0, conductivity of from about 580 to about 1570 µS/cm, oxidation-reduction potential of from about 200 to about 760 mV, temperature of from 15 to 30° C., linear liquid stream speed of from about 0.6 to about 1.03 meters per second, and liquid stream pressure of about 1 bar (approximately 14.5 psi). The flow of the liquid stream, when present, was from 1 to 2 gallons per minute.

For three minutes per day, the liquid stream was stopped from passing across the wetted surface of the flow cell, and the respective chemical treatment was pumped across the wetted surface of the flow cell at a rate of 10 gallons per day (i.e., 26.3 mL/min). After the three minutes, chemical treatment was stopped and the liquid stream resumed across the wetted surface of the flow cell.

Figure 10:
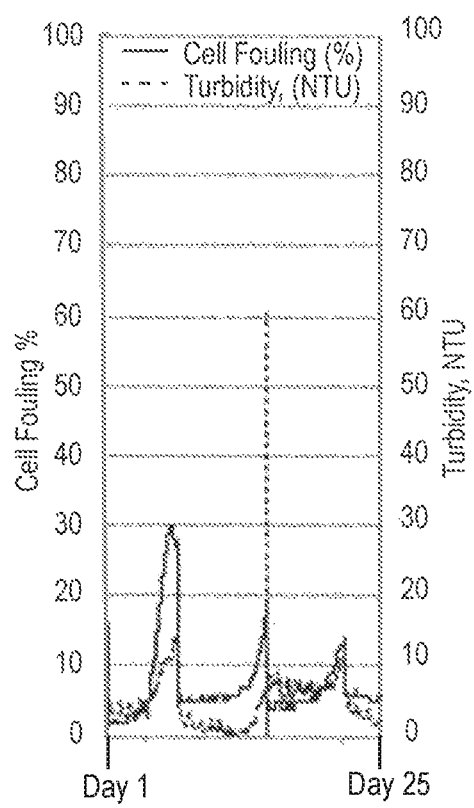
FIG. 10 is a plot of results related to treatment with a mineral acid-based cleaning solution of Example 3 herein.

As shown in FIG. 10, cell fouling was maintained at less than about 30% for approximately 25 days in the challenging high-fouling system of the present example by an acid cleaner comprising phosphoric and nitric acids.

Figure 11:
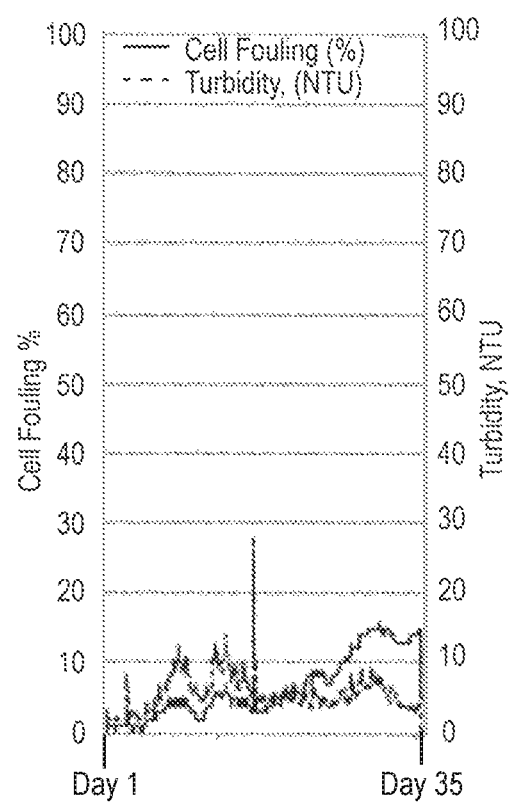
FIG. 11 is a plot of results related to treatment with a urea salt-based cleaning solution of Example 3 herein.

As shown in FIG. 11, cell fouling was maintained at less than about 15% for approximately 35 days in the challenging high-fouling system of the present example by a urea-based cleaner comprising urea hydrogen chloride.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Individual embodiments, or elements thereof, may comprise, consist of, or consist essentially of the recited elements, unless the context clearly indicates otherwise. In other words, any recitation of a statement such as "x comprises y" includes the recitations of "x consisting of y" and "x consisting essentially of y." Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method comprising:
    contacting an industrial water stream at an industrial water stream pressure with a plurality of surfaces utilized for measuring a plurality of parameters of an industrial water in an industrial water system;
    isolating a first subset of the surfaces from the industrial water stream while a second subset of the surfaces maintains contact with the industrial water stream;
    cleaning at least one surface of the first subset of surfaces while the second subset of surfaces maintains contact with the industrial water stream; and
    restoring contact of the industrial water stream with the first subset of surfaces;
    wherein the first subset of the surfaces comprises at least one of a wetted surface of a pH sensor, a wetted surface of an oxidation-reduction potential sensor, and a wetted surface of a light transference medium; and
    wherein the second subset of the surfaces comprises at least one of a wetted surface of a corrosion detection sensor and a wetted surface of a conductivity sensor.

2. The method of claim 1, wherein the cleaning comprises contacting a combined gaseous and liquid stream with the at least one surface of the first subset.

3. The method of claim 2, wherein the combined gaseous and liquid stream comprises a cleaning solution.

4. The method of claim 3, wherein the cleaning solution comprises aqueous urea hydrogen chloride.

5. The method of claim 3, wherein the cleaning solution comprises an ingredient selected from urea hydrogen chloride, phosphoric acid, sulfuric acid, nitric acid, a peroxyacid, a detergent, an emulsifier, or a combination thereof.

6. The method of claim 2, wherein a gaseous stream having a gaseous stream pressure is introduced into a liquid stream at a liquid stream pressure to form the combined gaseous and liquid stream.

7. The method of claim 6, wherein the gaseous stream pressure is from 10 to 100 psi greater than the liquid stream pressure.

8. The method of claim 6, wherein the gaseous stream is introduced in a direction perpendicular from the liquid stream.

9. The method of claim 6, wherein the gaseous stream comprises an acid gas selected from a carbon-containing acid gas, a sulfur-containing acid gas, a nitrogen-containing acid gas, a chlorine-containing acid gas, or a combination thereof.

10. The method of claim 6, wherein pellets of carbon dioxide are introduced with the gaseous stream into the liquid stream.

11. The method of claim 6, wherein the gaseous stream is introduced intermittently into the liquid stream.

12. The method of claim 2, wherein the combined gaseous and liquid stream comprises a gaseous substance selected from air, nitrogen, oxygen, an acid gas, or a combination thereof.

13. The method of claim 2, wherein the first subset of surfaces comprises a wetted surface of a light transference medium.

14. The method of claim 13, further comprising fanning the combined gaseous and liquid stream as it flows toward the wetted surface of the light transference medium.

15. The method of claim 1, wherein the cleaning comprises contacting a cleaning solution with the at least one surface of the first subset.

16. The method of claim 15, wherein the cleaning solution comprises aqueous urea hydrogen chloride.

17. The method of claim 15, wherein the cleaning solution comprises an ingredient selected from urea hydrogen chloride, phosphoric acid, sulfuric acid, nitric acid, a peroxyacid, a detergent, an emulsifier, or a combination thereof.

18. The method of claim 1, wherein the industrial water system is selected from a cooling water system, a heating water system, a papermaking system, a refining system, a chemical processing system, a crude oil extraction system, and a natural gas extraction system.

19. The method of claim 1, wherein the industrial water system is a cooling water system.

20. The method of claim 1, wherein at least one of the surfaces is located in a narrowed portion of the industrial water stream.

\* \* \* \* \*